United States Patent
Jiménez-Martínez et al.

(10) Patent No.: US 11,766,217 B2
(45) Date of Patent: Sep. 26, 2023

(54) SYSTEMS AND METHODS FOR MULTIMODAL POSE AND MOTION TRACKING FOR MAGNETIC FIELD MEASUREMENT OR RECORDING SYSTEMS

(71) Applicant: HI LLC, Los Angeles, CA (US)

(72) Inventors: Ricardo Jiménez-Martínez, Culver City, CA (US); Jamu Alford, Lake Arrowhead, CA (US); Geoffrey Iwata, Los Angeles, CA (US); Ethan Pratt, Santa Clara, CA (US)

(73) Assignee: HI LLC, Los Angeles, CA (US)

( * ) Notice: Subject to any disclaimer, the term of this patent is extended or adjusted under 35 U.S.C. 154(b) by 337 days.

(21) Appl. No.: 17/328,271

(22) Filed: May 24, 2021

(65) Prior Publication Data

US 2021/0369201 A1  Dec. 2, 2021

Related U.S. Application Data

(60) Provisional application No. 63/076,880, filed on Sep. 10, 2020, provisional application No. 63/076,015, (Continued)

(51) Int. Cl.
*A61B 5/00* (2006.01)
*A61B 5/246* (2021.01)
*G01R 33/26* (2006.01)

(52) U.S. Cl.
CPC ............ *A61B 5/6803* (2013.01); *A61B 5/246* (2021.01); *G01R 33/26* (2013.01); *A61B 2562/0223* (2013.01)

(58) Field of Classification Search
CPC .. A61B 5/00; A61B 5/24; A61B 5/242; A61B 5/245; A61B 5/246; A61B 5/68;
(Continued)

(56) References Cited

U.S. PATENT DOCUMENTS 3,173,082 A   3/1965   Bell et al.
3,257,608 A   6/1966   Bell et al.
(Continued)

FOREIGN PATENT DOCUMENTS

CN   104730484   6/2015
CN   107562188   1/2018
(Continued)

OTHER PUBLICATIONS

Zhang Xin et al: "Detection and analysis of MEG signals in occipital region with double channel OPM sensors", Journal of Neuroscience Methods, Elsevier Science Publisher B. V., Amsterdam, NL, vol. 346, Sep. 17, 2020 (Sep. 17, 2020).
(Continued)

*Primary Examiner* — Huy Q Phan
*Assistant Examiner* — David B Frederiksen
(74) *Attorney, Agent, or Firm* — Branch Partners PLLC; Bruce E. Black

(57) ABSTRACT

A magnetic field recording system includes a headgear to be placed on a user; optically pumped magnetometers (OPMs) disposed in or on the headgear to detect magnetic fields; at least two sensing modalities selected from the following: i) a magnetic sensing modality, ii) an optical sensing modality, or iii) an inertial sensing modality; and a tracking unit configured to receive, from each of the at least two sensing modalities, a corresponding magnetic data stream, optical data stream, or inertial data stream and to track a position or orientation of the headgear or user; and a system controller configured to control operation of the OPMs and to receive, from the tracking unit, the position or orientation of the headgear or user.

20 Claims, 6 Drawing Sheets

Related U.S. Application Data filed on Sep. 9, 2020, provisional application No. 63/052,327, filed on Jul. 15, 2020, provisional application No. 63/031,469, filed on May 28, 2020.

(58) Field of Classification Search
CPC .... A61B 5/6803; G01N 24/006; G01R 33/20; G01R 33/24; G01R 33/26
See application file for complete search history.

(56) References Cited

U.S. PATENT DOCUMENTS

| | | |
|---|---|---|
| 3,495,161 A | 2/1970 | Bell |
| 3,501,689 A | 3/1970 | Robbiano |
| 3,513,381 A | 5/1970 | Happer, Jr. |
| 4,193,029 A | 3/1980 | Cioccio et al. |
| 4,951,674 A | 8/1990 | Zanakis et al. |
| 5,189,368 A | 2/1993 | Chase |
| 5,192,921 A | 3/1993 | Chantry et al. |
| 5,225,778 A | 7/1993 | Chaillout et al. |
| 5,254,947 A | 10/1993 | Chaillout et al. |
| 5,309,095 A | 5/1994 | Ahonen et al. |
| 5,442,289 A | 8/1995 | Dilorio et al. |
| 5,444,372 A | 8/1995 | Wikswo, Jr. et al. |
| 5,471,985 A | 12/1995 | Warden |
| 5,506,200 A | 4/1996 | Hirschkoff et al. |
| 5,526,811 A | 6/1996 | Lypchuk |
| 5,713,354 A | 2/1998 | Warden |
| 6,144,872 A | 11/2000 | Graetz |
| 6,339,328 B1 | 1/2002 | Keene et al. |
| 6,472,869 B1 | 10/2002 | Upschulte et al. |
| 6,665,553 B2 | 12/2003 | Kandori et al. |
| 6,806,784 B2 | 10/2004 | Hollberg et al. |
| 6,831,522 B2 | 12/2004 | Kitching et al. |
| 7,038,450 B2 | 5/2006 | Romalis et al. |
| 7,102,451 B2 | 9/2006 | Happer et al. |
| 7,145,333 B2 | 12/2006 | Romalis et al. |
| 7,521,928 B2 | 4/2009 | Romalis et al. |
| 7,656,154 B2 | 2/2010 | Kawabata et al. |
| 7,826,065 B1 | 11/2010 | Okandan et al. |
| 7,872,473 B2 | 1/2011 | Kitching et al. |
| 7,994,783 B2 | 8/2011 | Ledbetter et al. |
| 8,054,074 B2 | 11/2011 | Ichihara et al. |
| 8,212,556 B1 | 7/2012 | Schwindt et al. |
| 8,258,884 B2 | 9/2012 | Borwick, III et al. |
| 8,319,156 B2 | 11/2012 | Borwick, III et al. |
| 8,334,690 B2 | 12/2012 | Kitching et al. |
| 8,373,413 B2 | 2/2013 | Sugioka |
| 8,405,389 B2 | 3/2013 | Sugioka et al. |
| 8,587,304 B2 | 11/2013 | Budker et al. |
| 8,836,327 B2 | 9/2014 | French et al. |
| 8,906,470 B2 | 12/2014 | Overstolz et al. |
| 8,941,377 B2 | 1/2015 | Mizutani et al. |
| 9,084,549 B2 | 7/2015 | Desain et al. |
| 9,095,266 B1 | 8/2015 | Fu |
| 9,116,201 B2 | 8/2015 | Shah et al. |
| 9,140,590 B2 | 9/2015 | Waters et al. |
| 9,140,657 B2 | 9/2015 | Ledbetter et al. |
| 9,169,974 B2 | 10/2015 | Parsa et al. |
| 9,244,137 B2 | 1/2016 | Kobayashi et al. |
| 9,291,508 B1 | 3/2016 | Biedermann et al. |
| 9,343,447 B2 | 3/2016 | Parsa et al. |
| 9,366,735 B2 | 6/2016 | Kawabata et al. |
| 9,383,419 B2 | 7/2016 | Mizutani et al. |
| 9,395,425 B2 | 7/2016 | Diamond et al. |
| 9,417,293 B2 | 8/2016 | Schaffer et al. |
| 9,429,918 B2 | 8/2016 | Parsa et al. |
| 9,568,565 B2 | 2/2017 | Parsa et al. |
| 9,575,144 B2 | 2/2017 | Komack et al. |
| 9,601,225 B2 | 3/2017 | Parsa et al. |
| 9,638,768 B2 | 5/2017 | Foley et al. |
| 9,639,062 B2 | 5/2017 | Dyer et al. |
| 9,677,905 B2 | 6/2017 | Waters et al. |
| 9,726,626 B2 | 8/2017 | Smith et al. |
| 9,726,733 B2 | 8/2017 | Smith et al. |
| 9,791,536 B1 | 10/2017 | Alem et al. |
| 9,829,544 B2 | 11/2017 | Bulatowicz |
| 9,846,054 B2 | 12/2017 | Waters et al. |
| 9,851,418 B2 | 12/2017 | Wolf et al. |
| 9,869,731 B1 | 1/2018 | Hovde et al. |
| 9,915,711 B2 | 3/2018 | Kornack et al. |
| 9,927,501 B2 | 3/2018 | Kim et al. |
| 9,948,314 B2 | 4/2018 | Dyer et al. |
| 9,964,609 B2 | 5/2018 | Ichihara et al. |
| 9,964,610 B2 | 5/2018 | Shah et al. |
| 9,970,999 B2 | 5/2018 | Larsen et al. |
| 9,995,800 B1 | 6/2018 | Schwindt et al. |
| 10,024,929 B2 | 7/2018 | Parsa et al. |
| 10,088,535 B1 | 10/2018 | Shah |
| 10,162,016 B2 | 12/2018 | Gabrys et al. |
| 10,194,865 B2 * | 2/2019 | Le ................... A61B 5/296 |
| 10,314,508 B2 * | 6/2019 | Desain ................ A61B 5/246 |
| 10,371,764 B2 | 8/2019 | Morales et al. |
| 10,772,561 B2 | 9/2020 | Donaldson |
| 2004/0232912 A1 | 11/2004 | Tsukamoto et al. |
| 2005/0007118 A1 | 1/2005 | Kitching et al. |
| 2005/0046851 A1 | 3/2005 | Riley, Jr. et al. |
| 2005/0206377 A1 | 9/2005 | Romalis et al. |
| 2007/0120563 A1 | 5/2007 | Kawabata et al. |
| 2007/0167723 A1 | 7/2007 | Park et al. |
| 2007/0205767 A1 | 9/2007 | Xu et al. |
| 2009/0079426 A1 | 3/2009 | Anderson |
| 2009/0101806 A1 | 4/2009 | Masuda |
| 2010/0219820 A1 | 9/2010 | Skidmore et al. |
| 2011/0062956 A1 | 3/2011 | Edelstein et al. |
| 2012/0112749 A1 | 5/2012 | Budker et al. |
| 2013/0082700 A1 | 4/2013 | Mizutani et al. |
| 2013/0082701 A1 | 4/2013 | Mizutani et al. |
| 2013/0265042 A1 | 10/2013 | Kawabata et al. |
| 2014/0121491 A1* | 5/2014 | Zhang .............. A61B 5/6814 |
| | | 600/409 |
| 2014/0306700 A1 | 10/2014 | Kamada et al. |
| 2014/0354275 A1 | 12/2014 | Sheng et al. |
| 2015/0022200 A1 | 1/2015 | Chihara et al. |
| 2015/0054504 A1 | 2/2015 | Ichihara et al. |
| 2015/0378316 A1 | 12/2015 | Parsa et al. |
| 2016/0061913 A1 | 3/2016 | Kobayashi et al. |
| 2016/0116553 A1 | 4/2016 | Kim et al. |
| 2016/0223627 A1 | 8/2016 | Shah et al. |
| 2016/0291099 A1 | 10/2016 | Ueno |
| 2016/0313417 A1 | 10/2016 | Kawabata et al. |
| 2017/0023653 A1 | 1/2017 | Kobayashi et al. |
| 2017/0023654 A1 | 1/2017 | Kobayashi et al. |
| 2017/0067969 A1 | 3/2017 | Butters et al. |
| 2017/0199138 A1 | 7/2017 | Parsa et al. |
| 2017/0261564 A1 | 9/2017 | Gabrys et al. |
| 2017/0331485 A1 | 11/2017 | Gobet et al. |
| 2017/0343617 A1 | 11/2017 | Manickam et al. |
| 2017/0343695 A1 | 11/2017 | Stetson et al. |
| 2017/0356969 A1 | 12/2017 | Jeno |
| 2017/0360322 A1 | 12/2017 | Jeno |
| 2017/0363695 A1 | 12/2017 | Jeno |
| 2018/0003777 A1 | 1/2018 | Sorenson et al. |
| 2018/0038921 A1 | 2/2018 | Parsa et al. |
| 2018/0100749 A1 | 4/2018 | Waters et al. |
| 2018/0128885 A1 | 5/2018 | Parsa et al. |
| 2018/0156875 A1 | 6/2018 | Herbsommer et al. |
| 2018/0219353 A1 | 8/2018 | Shah |
| 2018/0238974 A1 | 8/2018 | Shah et al. |
| 2018/0313908 A1 | 11/2018 | Knappe et al. |
| 2018/0313913 A1 | 11/2018 | DeNatale et al. |
| 2018/0372813 A1 | 12/2018 | Bulatowicz et al. |
| 2019/0391213 A1 | 12/2019 | Alford |
| 2020/0025844 A1 | 1/2020 | Alford et al. |
| 2020/0056263 A1* | 2/2020 | Bhattacharyya .......... C22B 5/16 |
| 2020/0057115 A1 | 2/2020 | Jiménez-Martínez et al. |
| 2020/0057116 A1 | 2/2020 | Zorzos et al. |
| 2020/0064421 A1 | 2/2020 | Kobayashi et al. |
| 2020/0072916 A1 | 3/2020 | Alford et al. |
| 2020/0088811 A1 | 3/2020 | Mohseni |
| 2020/0109481 A1 | 4/2020 | Sobek et al. |
| 2020/0123416 A1 | 4/2020 | Bhattacharyya et al. |
| 2020/0191883 A1 | 6/2020 | Bhattacharyya et al. |
| 2020/0241094 A1 | 7/2020 | Alford |
| 2020/0256929 A1 | 8/2020 | Ledbetter et al. |

(56) References Cited

U.S. PATENT DOCUMENTS

| | | |
|---|---|---|
| 2020/0309873 A1 | 10/2020 | Ledbetter et al. |
| 2020/0334559 A1 | 10/2020 | Anderson et al. |
| 2020/0341081 A1 | 10/2020 | Mohseni et al. |
| 2020/0381128 A1 | 12/2020 | Pratt et al. |
| 2020/0400763 A1 | 12/2020 | Pratt |
| 2021/0011094 A1 | 1/2021 | Bednarke |
| 2021/0015385 A1 | 1/2021 | Katnani et al. |
| 2021/0015427 A1 | 1/2021 | Shah et al. |
| 2021/0041512 A1 | 2/2021 | Pratt et al. |
| 2021/0041513 A1 | 2/2021 | Mohseni |
| 2021/0063510 A1 | 3/2021 | Ledbetter |

FOREIGN PATENT DOCUMENTS

| | | |
|---|---|---|
| CN | 110742607 | 2/2020 |
| CN | 110859610 | 3/2020 |
| EP | 2738627 A3 | 6/2014 |
| EP | 2380029 B1 | 10/2015 |
| EP | 3037836 B1 | 9/2017 |
| JP | 2016109665 | 6/2016 |
| JP | 2018004462 | 1/2018 |
| WO | 2005/081794 | 9/2005 |
| WO | 2014/031985 | 2/2014 |
| WO | 2017/095998 | 6/2017 |
| WO | 2020/084194 | 4/2020 |

OTHER PUBLICATIONS

Hill RM, Boto E, Holmes N, et al. A tool for functional brain imaging with lifespan compliance [published correction appears in Nat Commun. Dec. 4, 2019;10(1):5628]. Nat Commun. 2019; 10(1):4785. Published Nov. 5, 2019. doi:10.1038/s41467-019-12486-x.

Zetter, R., Iivanainen, J. & Parkkonen, L. Optical Co-registration of MRI and On-scalp MEG. Sci Rep 9, 5490 (2019). https://doi.org/10.1038/s41598-019-41763-4.

Garrido-Jurado, Sergio, Rafael Muñoz-Salinas, Francisco José Madrid-Cuevas and Manuel J. Marín-Jiménez. "Automatic generation and detection of highly reliable fiducial markers under occlusion." Pattern Recognit. 47 (2014): 2280-2292.

Hill RM, Boto E, Rea M, et al. Multi-channel whole-head OPM-MEG: Helmet design and a comparison with a conventional system [published online ahead of print, May 29, 2020]. Neuroimage. 2020;219:116995. doi:10.1016/j.neuroimage.2020.116995.

V. Kazemi and J. Sullivan, "One millisecond face alignment with an ensemble of regression trees," 2014 IEEE Conference on Computer Vision and Pattern Recognition, Columbus, OH, 2014, pp. 1867-1874, doi: 10.1109/CVPR.2014.241.

Holmes, N., Tierney, T.M., Leggett, J. et al. Balanced, bi-planar magnetic field and field gradient coils for field compensation in wearable magnetoencephalography. Sci Rep 9, 14196 (2019).

N. Holmes, J. Leggett, E. Boto, G. Roberts, R.M. Hill, T.M. Tierney, V. Shah, G.R. Barnes, M.J. Brookes, R. Bowtell A bi-planar coil system for nulling background magnetic fields in scalp mounted magnetoencephalography Neuroimage, 181 (2018), pp. 760-774.

J. M. Leger et. al., In-flight performance of the Absolute Scalar Magnetometer vector mode on board the Swarm satellites, Earth, Planets, and Space (2015) 67:57.

Alexandrov, E. B., Balabas, M. V., Kulyasov, V. N., Ivanov, A. E., Pazgalev, A. S., Rasson, J. L., . . . (2004). Three-component variometer based on a scalar potassium sensor. Measurement Science and Technology, 15(5), 918-922.

Gravrand, O., Khokhlov, A., & JL, L. M. (2001). On the calibration of a vectorial 4He pumped magnetometer. Earth, planets and space , 53 (10), 949-958.

Borna, Amir & Carter, Tony & Colombo, Anthony & Jau, Y-Y & McKay, Jim & Weisend, Michael & Taulu, Samu & Stephen, Julia & Schwindt, Peter. (2018). Non-Invasive Functional-Brain-Imaging with a Novel Magnetoencephalography System. 9 Pages.

Vrba J, Robinson SE. Signal processing in magnetoencephalography. Methods. 2001;25(2):249-271. doi:10.1006/meth.2001.1238.

Uusitalo M and Ilmoniemi R., 1997, Signal-space projection method for separating MEG or EEG into components. Med. Biol. Comput. (35) 135-140.

Taulu S and Kajola M., 2005, Presentation of electromagnetic multichannel data: the signal space separation method. J. Appl. Phys. (97) 124905 (2005).

Taulu S, Simola J and Kajola M., 2005, Applications of the signal space separation method. IEEE Trans. Signal Process. (53) 3359-3372 (2005).

Taulu S, Simola J., 2006, Spatiotemporal signal space separation method for rejecting nearby interference in MEG measurements. Phys. Med. Biol. (51) 1759-1768 (2006).

Johnson, et al., Magnetoencephalography with a two-color pump-probe, fiber-coupled atomic magnetometer, Applied Physics Letters 97, 243703 2010.

Zhang, et al., Magnetoencephalography using a compact multichannel atomic magnetometer with pump-probe configuration, AIP ADVANCES 8, 125028 (2018).

Xia, H. & Ben-Amar Baranga, Andrei & Hoffman, D. & Romalis, Michael. (2006). Magnetoencephalography with an atomic magnetometer. Applied Physics Letters—Appl Phys Lett. 89. 10.1063/1.2392722.

Ilmoniemi, R. (2009). The triangle phantom in magnetoencephalography. In 24th Annual Meeting of Japan Biomagnetism and Bioelecctromagnetics Society, Kanazawa, Japan, 28.29.5.2009 (pp. 6263).

Oyama D. Dry phantom for magnetoencephalography—Configuration, calibration, and contribution. J Neurosci Methods. 2015;251:24-36. doi: 0.1016/j.jneumeth.2015.05.004.

Chutani, R., Maurice, V., Passilly, N. et al. Laser light routing in an elongated micromachined vapor cell with diffraction gratings for atomic clock applications. Sci Rep 5, 14001 (2015). https://doi.org/10.1038/srep14001.

Eklund, E. Jesper, Andrei M. Shkel, Svenja Knappe, Elizabeth A. Donley and John Kitching. "Glass-blown spherical microcells for chip-scale atomic devices." (2008).

Jiménez-Martinez R, Kennedy DJ, Rosenbluh M, et al. Optical hyperpolarization and NMR detection of 129Xe on a microfluidic chip. Nat Commun. 2014;5:3908. Published May 20, 2014. doi:10.1038/ncomms4908.

Boto, Elena, Sofie S. Meyer, Vishal Shah, Orang Alem, Svenja Knappe, Peter Kruger, T. Mark Fromhold, et al. "A New Generation of Magnetoencephalography: Room Temperature Measurements Using Optically-Pumped Magnetometers." NeuroImage 149 (Apr. 1, 2017): 404-14.

Bruno, A. C., and P. Costa Ribeiro. "Spatial Fourier Calibration Method for Multichannel SQUID Magnetometers." Review of Scientific Instruments 62, No. 4 (Apr. 1, 1991): 1005-9.

Chella, Federico, Filippo Zappasodi, Laura Marzetti, Stefania Della Penna, and Vittorio Pizzella. "Calibration of a Multichannel MEG System Based on the Signal Space Separation Method." Physics in Medicine and Biology 57 (Jul. 13, 2012): 4855-70.

Pasquarelli, A, M De Melis, Laura Marzetti, Hans-Peter Müller, and S N Erné. "Calibration of a Vector-MEG Helmet System." Neurology & Clinical Neurophysiology□: NCN 2004 (Feb. 1, 2004): 94.

Pfeiffer, Christoph, Lau M. Andersen, Daniel Lundqvist, Matti Hämäläinen, Justin F. Schneiderman, and Robert Oostenveld. "Localizing On-Scalp MEG Sensors Using an Array of Magnetic Dipole Coils." PLOS ONE 13, No. 5 (May 10, 2018): e0191111.

Vivaldi, Valentina, Sara Sommariva, and Alberto Sorrentino. "A Simplex Method for the Calibration of a MEG Device." Communications in Applied and Industrial Mathematics 10 (Jan. 1, 2019): 35-46.

Nagel, S., & Spüler, M. (2019). Asynchronous non-invasive high-speed BCI speller with robust non-control state detection. Scientific Reports, 9(1), 8269.

Thielen, J., van den Broek, P., Farquhar, J., & Desain, P. (2015). Broad-Band Visually Evoked Potentials: Re(con) volution in Brain-Computer Interfacing. PloS One, 10(7), e0133797. https://doi.org/10.1371/journal.pone.0133797.

J. Kitching, "Chip-scale atomic devices," Appl. Phys. Rev. 5(3), 031302 (2018), 39 pages.

(56) References Cited

OTHER PUBLICATIONS

Allred, J. C., Lyman, R. N., Kornack, T. W., & Romalis, M. V. (2002). High-sensitivity atomic magnetometer unaffected by spin-exchange relaxation. Physical review letters, 89(13), 130801.

Balabas et al. Polarized alkali vapor with minute-long transverse spin-relaxation time, Phys. Rev. Lett. 105, 070801—Published Aug. 12, 2010.

Barbieri, F., Trauchessec, V., Caruso, L., Trejo-Rosillo, J., Telenczuk, B., Paul, E., . . . & Ouanounou, G. (2016). Local recording of biological magnetic fields using Giant Magneto Resistance-based micro-probes. Scientific reports, 6, 39330.

Dmitry Budker and Michael Romalis, "Optical Magnetometry," Nature Physics, 2008, https://arxiv.org/abs/physics/0611246v1.

Anthony P. Colombo, Tony R. Carter, Amir Borna, Yuan-Yu Jau, Cort N. Johnson, Amber L. Dagel, and Peter D. D. Schwindt, "Four-channel optically pumped atomic magnetometer for magnetoencephalography," Opt. Express 24, 15403-15416 (2016).

Dang, H.B. & Maloof, A.C. & Romalis, Michael. (2009). Ultra-high sensitivity magnetic field and magnetization measurements with an atomic magnetometer. Applied Physics Letters. 97. 10.1063/1.3491215.

Donley, E.A. & Hodby, E & Hollberg, L & Kitching, J. (2007). Demonstration of high-performance compact magnetic shields for chip-scale atomic devices. The Review of scientific instruments. 78. 083102.

Hämäläinen, Matti & Hari, Riitta & Ilmoniemi, Risto J. & Knuutila, Jukka & Lounasmaa, Olli V. Apr. 1993. Magnetoencephalograph—theory, instrumentation, and applications to noninvasive studies of the working human brain. Reviews of Modern Physics. vol. 65, Issue 2. 413-497.

Hunter, D. and Piccolomo, S. and Pritchard, J. D. and Brockie, N. L. and Dyer, T. E. and Riis, E. (2018) Free-induction-decay magnetometer based on a microfabricated Cs vapor cell. Physical Review Applied (10). ISSN 2331-7019.

Jiménez-Martínez, R., Griffith, W. C., Wang, Y. J., Knappe, S., Kitching, J., Smith, K., & Prouty, M. D. (2010). Sensitivity comparison of Mx and frequency-modulated bell-bloom Cs magnetometers in a microfabricated cell. IEEE Transactions on Instrumentation and Measurement, 59(2), 372-378.

Kiwoong Kim, Samo Begus, Hui Xia, Seung-Kyun Lee, Vojko Jazbinsek, Zvonko Trontelj, Michael V. Romalis, Multi-channel atomic magnetometer for magnetoencephalography: A configuration study. NeuroImage 89 (2014) 143-151 http://physics.princeton.edu/romalis/papers/Kim_2014.pdf.

Knappe, Svenja & Sander, Tilmann & Trahms, Lutz. (2012). Optically-Pumped Magnetometers for MEG. Magnetoencephalography: From Signals to Dynamic Cortical Networks. 993-999. 10.1007/978-3-642-33045-2_49.

Kominis, I.K., Kornack, T.W., Allred, J.C. and Romalis, M.V., 2003. A subfemtotesla multichannel atomic magnetometer. Nature, 422(6932), p. 596.

Korth, H., K. Strohbehn, F. Tejada, A. G. Andreou, J. Kitching, S. Knappe, B. J. Lehtonen, S. M. London, and M. Kafel (2016), Miniature atomic scalarmagnetometer for space based on the rubidium isotope 87Rb, J. Geophys. Res. Space Physics, 121, 7870-7880, doi: 10.1002/2016JA022389.

Lenz, J. and Edelstein, S., 2006. Magnetic sensors and their applications. IEEE Sensors journal, 6(3), pp. 631-649.

Li, S & Vachaspati, Pranjal & Sheng, Dehong & Dural, Nezih & Romalis, Michael. (2011). Optical rotation in excess of 100 rad generated by Rb vapor in a multipass cell. Phys. Rev. A. 84. 10.1103/PhysRevA.84.061403.

Maze, J. R., Stanwix, P. L., Hodges, J. S., Hong, S., Taylor, J. M., Cappellaro, P., . . . & Yacoby, A. (2008). Nanoscale magnetic sensing with an individual electronic spin in diamond. Nature, 455(7213), 644.

Sander TH, Preusser J, Mhaskar R, Kitching J, Trahms L, Knappe S. Magnetoencephalography with a chip-scale atomic magnetometer. Biomed Opt Express. 2012;3(5):981-90.

J. Seltzer, S & Romalis, Michael. (2010). High-temperature alkali vapor cells with antirelaxation surface coatings. Journal of Applied Physics. 106. 114905-114905. 10.1063/1.3236649.

Seltzer, S. J., and Romalis, M.V., "Unshielded three-axis vector operation of a spin-exchange-relaxation-free atomic magnetometer." Applied physics letters 85.20 (2004): 4804-4806.

Sheng, Dong & R. Perry, Abigail & Krzyzewski, Sean & Geller, Shawn & Kitching, John & Knappe, Svenja. (2017). A microfabricated optically-pumped magnetic gradiometer. Applied Physics Letters. 110. 10.1063/1.4974349.

Sheng, Dehong & Li, S & Dural, Nezih & Romalis, Michael. (2013). Subfemtotesla Scalar Atomic Magnetometry Using Multipass Cells. Physical review letters. 110. 160802. 10.1103/PhysRevLett.110.160802.

Volkmar Schultze et al. An Optically Pumped Magnetometer Working in the Light-Shift Dispersed Mz Mode, Sensors 2017, 17, 561; doi:10.3390/s17030561.

Fang, J. and Qin, J., 2012. In situ triaxial magnetic field compensation for the spin-exchange-relaxation-free atomic magnetometer. Review of Scientific Instruments, 83(10), p. 103104.

Joon Lee, Hyun & Shim, Jeong & Moon, Han Seb & Kim, Kiwoong. (2014). Flat-response spin-exchange relaxation free atomic magnetometer under negative feedback. Optics Express. 22. 10.1364/OE.22.019887.

Griffith, Clark & Jimenez-Martinez, Ricardo & Shah, Vishal & Knappe, Svenja & Kitching, John. (2009). Miniature atomic magnetometer integrated with flux concentrators. Applied Physics Letters—Appl Phys Lett. 94. 10.1063/1.3056152.

Lee, S.-K & Romalis, Michael. (2008). Calculation of Magnetic Field Noise from High-Permeability Magnetic Shields and Conducting Objects with Simple Geometry. Journal of Applied Physics. 103. 084904-084904. 10.1063/1.2885711.

Vovrosh, Jamie & Voulazeris, Georgios & Petrov, Plamen & Zou, Ji & Gaber Beshay, Youssef & Benn, Laura & Woolger, David & Attallah, Moataz & Boyer, Vincent & Bongs, Kai & Holynski, Michael. (2018). Additive manufacturing of magnetic shielding and ultra-high vacuum flange for cold atom sensors. Scientific Reports. 8. 10.1038/s41598-018-20352-x.

Kim, Young Jin & Savukov, I. (2016). Ultra-sensitive Magnetic Microscopy with an Optically Pumped Magnetometer. Scientific Reports. 6. 24773. 10.1038/srep24773.

Navau, Carles & Prat-Camps, Jordi & Sanchez, Alvaro. (2012). Magnetic Energy Harvesting and Concentration at a Distance by Transformation Optics. Physical review letters. 109. 263903. 10.1103/PhysRevLett.109.263903.

Orang Alem, Rahul Mhaskar, Ricardo Jimenez-Martinez, Dong Sheng, John LeBlanc, Lutz Trahms, Tilmann Sander, John Kitching, and Svenja Knappe, "Magnetic field imaging with microfabricated optically-pumped magnetometers," Opt. Express 25, 7849-7858 (2017).

Slocum et al., Self-Calibrating Vector Magnetometer for Space, https://esto.nasa.gov/conferences/estc-2002/Papers/B3P4(Slocum).pdf.

Dupont-Roc, J & Haroche, S & Cohen-Tannoudji, C. (1969). Detection of very weak magnetic fields (10-9gauss) by 87Rb zero-field level crossing resonances. Physics Letters A—Phys Lett A. 28. 638-639. 10.1016/0375-9601(69)90480-0.

J. A. Neuman, P. Wang, and A. Gallagher, Robust high-temperature sapphire cell for metal vapors, Review of Scientific Instruments, vol. 66, Issue 4, Apr. 1995, pp. 3021-3023.

Borna, Amir, et al. "A 20-channel magnetoencephalography system based on optically pumped magnetometers." Physics in Medicine & Biology 62.23 (2017): 8909.

R. E. Slocum & L. J. Ryan, Design and operation of the minature vector laser magnetometer, Nasa Earth Science Technology Conference 2003.

Schoenmaker, Jeroen & R Pirota, K & Teixeira, Julio. (2013). Magnetic flux amplification by Lenz lenses. The Review of scientific instruments. 84. 085120. 10.1063/1.4819234.

Hu, Yanhui & Hu, Zhaohui & Liu, Xuejing & Li, Yang & Zhang, Ji & Yao, Han & Ding, Ming. (2017). Reduction of far off-resonance laser frequency drifts based on the second harmonic of electro-optic

(56) References Cited

OTHER PUBLICATIONS modulator detection in the optically pumped magnetometer. Applied Optics. 56. 5927. 10.1364/AO.56.005927.
Masuda, Y & Ino, T & Skoy, Vadim & Jones, G.L. (2005). 3He polarization via optical pumping in a birefringent cell. Applied Physics Letters. 87. 10.1063/1.2008370.
A.B. Baranga et al., An atomic magnetometer for brain activity imaging, Real Time Conference 2005. 14th IEEE-NPSS. pp. 417-418.
Larry J. Ryan, Robert E. Slocum, and Robert B. Steves, Miniature Vector Laser Magnetometer Measurements of Earth's Field, May 10, 2004, 4 pgs.
Lorenz, V. O., Dai, X., Green, H., Asnicar, T. R., & Cundiff, S. T. (2008). High-density, high-temperature alkali vapor cell. Review of Scientific Instruments, 79(12), 4 pages.
F. Jackson Kimball, D & Dudley, J & Li, Y & Thulasi, Swecha & Pustelny, Szymon & Budker, Dmitry & Zolotorev, Max. (2016). Magnetic shielding and exotic spin-dependent interactions. Physical Review D. 94. 10.1103/PhysRevD.94.082005.
Huang, Haichao, et al. "Single-beam three-axis atomic magnetometer." Applied Physics Letters 109.6 (2016): 062404. (Year: 2016).
Scott Jeffrey Seltzer: "Developments in alkali-metal atomic magnetometry", Nov. 1, 2008 (Nov. 1, 2008), XP055616618, ISBN: 978-0-549-93355-7 Retrieved from the Internet: URL:http://physics.princeton.edu/atomic/romalis/papers/Seltzer%20Thesis.pdf [retrieved on Aug. 29, 2019] pp. 148-159.
Haifeng Dong et al: "Atomic-Signal-Based Zero-Field Finding Technique for Unshielded Atomic Vector Magnetometer", IEEE Sensors Journal, IEEE Service Center, New York, NY, US, vol. 13, No. 1, Jan. 1, 2013 (Jan. 1, 2013), pp. 186-189.
Boto, E, Holmes, N, Leggett, J, Roberts, G, Shah, V, Meyer, SS, Muñoz, LD, Mullinger, KJ, Tierney, TM, Bestmann, S, Barnes, GR, Bowtell, R & Brookes, MJ 2018, 'Moving magnetoencephalography towards real world applications with a wearable system', Nature, vol. 555, pp. 657-661.
Ijsselsteijn, R & Kielpinski, Mark & Woetzel, S & Scholtes, Theo & Kessler, Ernst & Stolz, Ronny & Schultze, V & Meyer, H-G. (2012). A full optically operated magnetometer array: An experimental study. The Review of scientific instruments. 83. 113106. 10.1063/1.4766961.
Tierney, T. M., Holmes, N., Meyer, S. S., Boto, E., Roberts, G., Leggett, J., . . . Barnes, G. R. (2018). Cognitive neuroscience using wearable magnetometer arrays: Non-invasive assessment of language function. NeuroImage, 181, 513-520.
Manon Kok, Jeroen D. Hol and Thomas B. Schon (2017), "Using Inertial Sensors for Position and Orientation Estimation", Foundations and Trends in Signal Processing: vol. 11: No. 1-2, pp. 1-153. http://dx.doi.org/10.1561/2000000094.
Okada, Y.C., Lahteenmaki, A. and Xu, C., "Experimental analysis of distortion of magnetoencephalography signals by the skull." Clinical neurophysiology 110 (2), 230-238 (1999).
Robinson, J.T., Pohlmeyer, E., Gather, M.C., Kemere, C., Kitching, J.E., Malliaras, G.G., Marblestone, A., Shepard, K. L., Stieglitz, T. and Xie, C., "Developing Next-Generation Brain Sensing Technologies—A Review." IEEE sensors journal, 19(22), 10163-10175 (2019).
Shah, V., Knappe, S., Schwindt, P.D. and Kitching, J., "Subpicotesla atomic magnetometry with a microfabricated vapour cell." Nature Photon 1, 649-652 (2007).
Griffith, W.C., Knappe, S. and Kitching, J., "Femtotesla atomic magnetometry in a microfabricated vapor cell." Optics express 18, (26), 27167-27172 (2010).
Tierney, T.M., Holmes, N., Mellor, S., López, J.D., Roberts, G., Hill, R.M., Boto, E., Leggett, J., Shah, V., Brookes, M.J. and Bowtell, R., "Optically pumped magnetometers: From quantum origins to multichannel magnetoencephalography." NeuroImage, 199, 598-608 (2019).
Iivanainen, J., Zetter, R., Grön, M., Hakkarainen, K. and Parkkonen, L., "On-scalp MEG system utilizing an actively shielded array of optically-pumped magnetometers." Neuroimage 194, 244-258 (2019).
Iivanainen, J., Stenroos, M. and Parkkonen, L., "Measuring MEG closer to the brain: Performance of on-scalp sensor arrays." NeuroImage 147, 542-553 (2017).
Kitching, J., Knappe, S., Gerginov, V., Shah, V., Schwindt, P.D., Lindseth, B., Donley E.A., "Chip-scale atomic devices: precision atomic instruments based on MEMS." In Frequency Standards And Metrology, 445-453 (2009).
Kitching, J., Knappe, S. and Donley, E.A., "Atomic sensors-a review." IEEE Sensors Journal, 11(9), 1749-1758 (2011).
Budker, D. and Romalis, M., "Optical magnetometry". Nature physics, 3(4), 227-234 (2007).
Happer, W., "Optical pumping", Rev. Mod. Phys., 44 (2), 169-249 (1972).
Purcell, E.M., Field, G.B., "Influence of collisions upon population of hyperfine states in hydrogen", Astrophys. J., 124, 542 (1956).
Ledbetter, M.P., Savukov, I.M., Acosta, V.M., Budker, D. and Romalis, M.V., "Spin-exchange-relaxation-free magnetometry with Cs vapor." Physical Review A, 77(3), 033408 (2008).
Bloom, A. L., "Principles of operation of the rubidium vapor magnetometer." Applied Optics 1(1), 61-68 (1962).
Bell, W.E., and Bloom, A.L., "Optically driven spin precession." Physical Review Letters 6, (6), 280 (1961).
Roberts, G., Holmes, N., Alexander, N., Boto, E., Leggett, J., Hill, R.M., Shah, V., Rea, M., Vaughan, R., Maguire, E.A. and Kessler, K., "Towards OPM-MEG in a virtual reality environment." NeuroImage, 199, 408-417 (2019).
Zhang, R., Xiao, W., Ding, Y., Feng, Y., Peng, X., Shen, L., Sun, C., Wu, T., Wu, Y., Yang, Y. and Zheng, Z., "Recording brain activities in unshielded Earth's field with optically pumped atomic magnetometers." Science Advances, 6(24) (2020).
De Cheveigné, A., Wong, D.D., Di Liberto, G.M., Hjortkjaer, J., Slaney, M. and Lalor, E., "Decoding the auditory brain with canonical component analysis." NeuroImage, 172, 206-216 (2018).
Mellinger, J., Schalk, G., Braun, C., Preissl, H., Rosenstiel, W., Birbaumer, N. and Kübler, A., "An MEG-based brain-computer interface (BCI)." Neuroimage, 36(3), 581-593 (2007).
Wolpaw, J.R., McFarland, D.J., Neat, G.W. and Forneris, C.A., "An EEG-based brain-computer interface for cursor control." Electroencephalography and clinical neurophysiology, 78(3), 252-259 (1991).
Lightfoot, G., "Summary of the N1-P2 cortical auditory evoked potential to estimate the auditory threshold in adults". Seminars in hearing, 37(1), 1 (2016).
Virtanen, J., Ahveninen, J., Ilmoniemi, R. J., Näätänen, R., & Pekkonen, E., "Replicability of MEG and EEG measures of the auditory N1/N1m-response." Electroencephalography and Clinical Neurophysiology/Evoked Potentials Section, 108(3), 291-298 (1998).
Gascoyne, L., Furlong, P. L., Hillebrand, A., Worthen, S. F., & Witton, C., "Localising the auditory N1m with event-related beamformers: localisation accuracy following bilateral and unilateral stimulation." Scientific reports, 6(1), 1-9 (2016).
Borna, A., Carter, T.R., Goldberg, J.D., Colombo, A.P., Jau, Y.Y., Berry, C., Mckay, J., Stephen, J., Weisend, M. and Schwindt, P.D., "A 20-channel magnetoencephalography system based on optically pumped magnetometers." Physics In Medicine & Biology, 62(23), 8909 (2017).
Pyragius, T., Marin Florez, H., & Fernholz, T. (2019). A Voigt effect based 3D vector magnetometer. Physical Review A, 100(2), https://doi.org/10.1103/PhysRevA.100.023416.
Rui Zhang, Rahul Mhaskar, Ken Smith, Easswar Balasubramaniam, Mark Prouty. "All Optical Scalar Atomic Magnetometer Capable of Vector Measurement," Submitted on Nov. 17, 2020. https://arxiv.org/abs/2011.08943; Geometrics, Inc., San Jose, CA, 95131, USA.
Arjen Stolk, Ana Todorovic, Jan-Mathijs Schoffelen, and Robert Oostenveld. "Online and offline tools for head movement compensation in MEG." Neuroimage 68 (2013): 39-48.
Bagherzadeh, Yasaman, Daniel Baldauf, Dimitrios Pantazis, and Robert Desimone. "Alpha synchrony and the neurofeedback control of spatial attention." Neuron 105, No. 3 (2020): 577-587.

\* cited by examiner

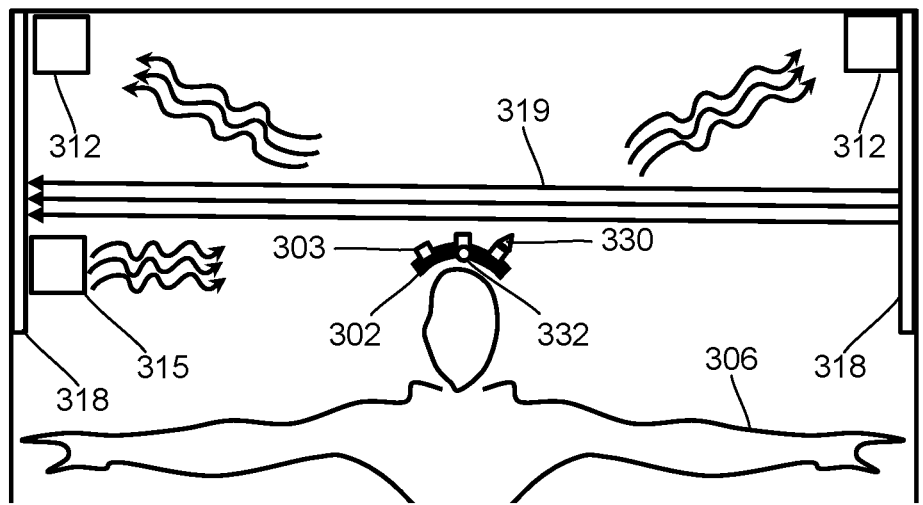
Fig. 4A
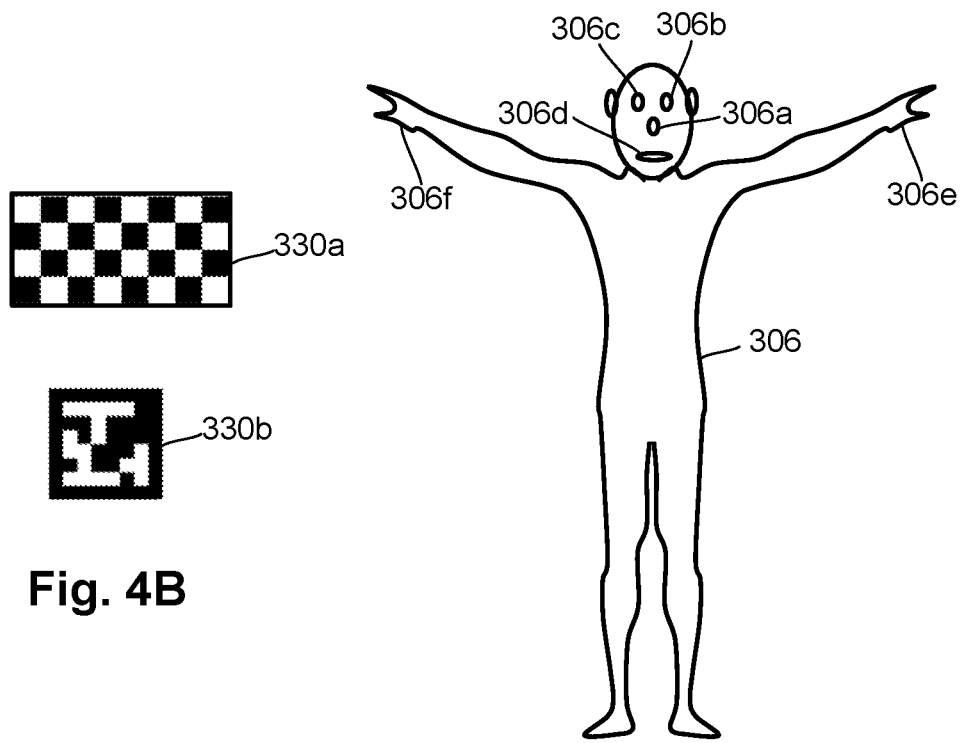
Fig. 4B
Fig. 4C

SYSTEMS AND METHODS FOR MULTIMODAL POSE AND MOTION TRACKING FOR MAGNETIC FIELD MEASUREMENT OR RECORDING SYSTEMS

CROSS-REFERENCE TO RELATED APPLICATIONS

This application claims the benefit of U.S. Provisional Patent Application Ser. No. 63/031,469, filed May 28, 2020; 63/052,327, filed Jul. 15, 2020; 63/076,015, filed Sep. 9, 2020; and 63/076,880, filed Sep. 10, 2020, all of which are incorporated herein by reference in their entireties.

FIELD

The present disclosure is directed to the area of magnetic field measurement or recording systems including systems for magnetoencephalography (MEG). The present disclosure is also directed to methods and systems for pose (e.g., position or orientation or both) and motion tracking for a MEG or other magnetic field measurement or recording system.

BACKGROUND

Magnetoencephalography (MEG) technologies measure brain activity by recording magnetic fields produced by electrical currents occurring naturally in the brain. In many instances, MEG instrumentation, based on superconducting quantum interference devices (SQUIDs) and optically pumped magnetometers (OPMs), is currently limited to applications in unnatural, research-grade environments. For instance, SQUID-MEG systems typically severely restrict head movement, limiting the type of tasks that can be performed by a subject. While OPM-MEG systems have enabled some degree of user motion their operation typically remains confined to enclosures formed by multiple layers of magnetic shielding material.

BRIEF SUMMARY

One embodiment is a magnetic field recording system that includes a headgear configured to be placed on a user; optically pumped magnetometers (OPMs) disposed in or on the headgear and configured to detect magnetic fields; at least two sensing modalities selected from the following: i) a magnetic sensing modality including at least one electromagnetic coil configured to produce magnetic field tones at one or more frequencies and at least one magnetic field sensor configured for placement on the user to detect the magnetic field tones and to produce a magnetic data stream, ii) an optical sensing modality including at least one light source and at least one camera or light detector configured to receive light reflected or directed from the user and to produce an optical data stream, or iii) an inertial sensing modality including at least one inertial sensor configured for placement on a user and to produce an inertial data stream; and a tracking unit configured to receive, from each of the at least two sensing modalities, the corresponding magnetic data stream, optical data stream, or inertial data stream and to track a position or orientation of the headgear or user; and a system controller configured to control operation of the OPMs and to receive, from the tracking unit, the position or orientation of the headgear or user.

In at least some embodiments, the at least two sensing modalities include the inertial sensing modality. In at least some embodiments, the at least two sensing modalities include the magnetic sensing modality, the optical sensing modality, and the inertial sensing modality.

In at least some embodiments, the magnetic field recording system further includes a passively shielded enclosure including a plurality of walls defining the passively shielded enclosure, each of the plurality of walls including passive magnetic shielding material to reduce an ambient background magnetic field within the passively shielded enclosure. In at least some embodiments, the magnetic field recording system further includes a plurality of active shield coils distributed within the passively shielded enclosure and configured to further reduce the ambient background magnetic field within the passively shielded enclosure. In at least some embodiments, at least one of the active shield coils is at least one of the at least one electromagnetic coil configured to produce the magnetic field tones. In at least some embodiments, the at least one electromagnetic coil is configured to produce the magnetic field tones having a frequency of at least 100 Hz.

In at least some embodiments, the optical sensing modality includes at least one fiducial marker for placement on the user, the headgear, or the OPM modules and configured to reflect light from the at least one light source. In at least some embodiments, the at least one fiducial marker is disposed on the headgear or the OPM modules. In at least some embodiments, at least one of the at least one light source is a fiducial marker for placement on the user, the headgear, or the OPM modules and configured to emit light.

In at least some embodiments, the tracking unit is configured to utilize at least one of the OPM modules as a fiduciary marker for the optical sensing modality. In at least some embodiments, the tracking unit is configured to utilize at least one feature of the user as a fiduciary marker for the optical sensing modality. In at least some embodiments, each of the at least one inertial sensor is an accelerometer or a gyroscope.

Another embodiment is a method of recording biomagnetic fields using any of the magnetic field recording systems described above. The method includes disposing the headgear on the user; tracking the position or orientation of the user, helmet, or OPM modules using the at least two sensing modalities and the tracking unit; recording the biomagnetic fields using the OPMs; and associating the biomagnetic fields with biological regions of the user using the tracked position or orientation.

In at least some embodiments, recording the biomagnetic fields includes recording the biomagnetic fields at individual first periods of time, wherein the at least two sensing modalities include the magnetic sensing modality, wherein tracking the position or orientation of the user includes generating the magnetic field tones using the at least one electromagnetic coil at second periods of time between the periods of time.

In at least some embodiments, the at least two sensing modalities include the magnetic sensing modality, wherein tracking the position or orientation of the user, helmet, or OPM modules includes generating the magnetic field tones at a frequency of at least 100 Hz using the at least one electromagnetic coil. In at least some embodiments, generating the magnetic field tones occurs, at least in part, simultaneously with recording the biomagnetic fields.

In at least some embodiments, the at least two sensing modalities includes the optical sensing modality, wherein tracking the position or orientation of the user, helmet, or OPM modules includes receiving light reflected or directed from the user at the at least one camera or light detector, wherein receiving the light occurs, at least in part, simultaneously with recording the biomagnetic fields.

In at least some embodiments, the at least two sensing modalities includes the inertial sensing modality, wherein tracking the position or orientation of the user, helmet, or OPM modules includes producing an inertial data stream using the at least one inertial sensor, wherein producing the inertial data stream occurs, at least in part, simultaneously with recording the biomagnetic fields.

In at least some embodiments, associating the biomagnetic fields with biological regions of the user includes sending estimates of the position or orientation of the user, helmet, or OPM modules from the tracking unit to the system controller.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4A is a schematic side view of one embodiment of components of a tracking arrangement for a magnetoencephalography (MEG) or other magnetic field measurement system including a passively shielded enclosure, according to the invention;

FIG. 4B illustrates embodiments of a fiducial marker for the tracking arrangement of FIG. 4A, according to the invention;

FIG. 4C illustrates features of a user that may be used as fiducial markers in the tracking arrangement of FIG. 4A, according to the invention;

DETAILED DESCRIPTION

Figure 1A:
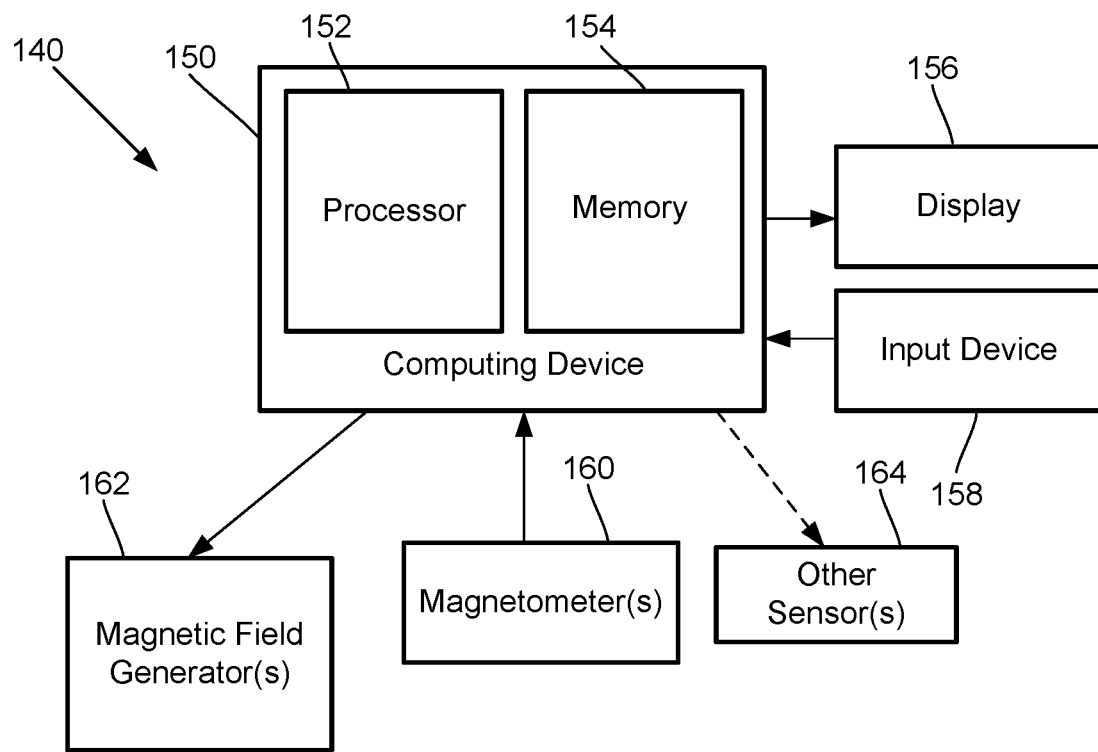
FIG. 1A is a schematic block diagram of one embodiment of a magnetic field measurement system, according to the invention.

The present disclosure is directed to the area of magnetic field measurement or recording systems including systems for magnetoencephalography (MEG). The present disclosure is also directed to methods and systems for pose (e.g., position or orientation or both) and motion tracking for a MEG or other magnetic field measurement or recording system.

Herein the terms "ambient background magnetic field" and "background magnetic field" are interchangeable and used to identify the magnetic field or fields associated with sources other than the magnetic field measurement or recording system and the magnetic field sources of interest, such as biological source(s) (for example, neural signals from a user's brain) or non-biological source(s) of interest. The terms can include, for example, the Earth's magnetic field, as well as magnetic fields from magnets, electromagnets, electrical devices, and other signal or field generators in the environment, except for the magnetic field generator(s) that are part of the magnetic field measurement or recording system.

The terms "gas cell", "vapor cell", and "vapor gas cell" are used interchangeably herein. Below, a vapor cell containing alkali metal vapor is described, but it will be recognized that other vapor cells can contain different gases or vapors for operation.

The methods and systems are described herein using optically pumped magnetometers (OPMs), but it will be understood that other magnetic field measurement devices, such as SQUIDs, can be used as an alternative to, or in addition to, OPMs. While there are many types of OPMs, in general magnetometers operate in two modalities: vector mode and scalar mode. In vector mode, the OPM can measure one, two, or all three vector components of the magnetic field; while in scalar mode the OPM can measure the total magnitude of the magnetic field.

Vector mode magnetometers measure a specific component of the magnetic field, such as the radial and tangential components of magnetic fields with respect the scalp of the human head. Vector mode OPMs often operate at zero-field and may utilize a spin exchange relaxation free (SERF) mode to reach femto-Tesla sensitivities. A SERF mode OPM is one example of a vector mode OPM, but other vector mode OPMs can be used at higher magnetic fields. These SERF mode magnetometers can have high sensitivity but may not function in the presence of magnetic fields higher than the linewidth of the magnetic resonance of the atoms of about 10 nT, which is much smaller than the magnetic field strength generated by the Earth.

Magnetometers operating in the scalar mode can measure the total magnitude of the magnetic field. (Magnetometers in the vector mode can also be used for magnitude measurements.) Scalar mode OPMs often have lower sensitivity than SERF mode OPMs and are capable of operating in higher magnetic field environments.

The magnetic field measurement or recording systems, such as a biological signal detection systems, described herein can be used to measure or observe electromagnetic signals (e.g., biomagnetic signals) generated by one or more magnetic field sources (for example, neural signals or other biological sources) of interest. The system can measure biologically generated magnetic fields and, at least in some embodiments, can measure biologically generated magnetic fields in an unshielded or partially shielded environment. Aspects of a magnetic field measurement or recording system will be exemplified below using magnetic signals from the brain of a user; however, biological signals from other areas of the body, as well as non-biological signals, can be measured using the system.

A magnetic field measurement or recording system, such as a biological signal detection system, can utilize one or more magnetic field sensors. Magnetometers will be used herein as an example of magnetic field sensors, but other magnetic field sensors may also be used. FIG. 1A is a block diagram of components of one embodiment of a magnetic field measurement or recording system 140 (such as a biological signal detection system.) The system 140 can include a computing device 150 or any other similar device that includes a processor 152, a memory 154, a display 156, an input device 158, one or more magnetometers 160 (for example, an array of magnetometers) which can be OPMs, one or more magnetic field generators 162, and, optionally, one or more other sensors 164 (e.g., non-magnetic field sensors). The system 140 and its use and operation will be described herein with respect to the measurement of neural signals arising from one or more magnetic field sources of interest in the brain of a user as an example. It will be understood, however, that the system can be adapted and used to measure signals from other magnetic field sources of interest including, but not limited to, other neural signals, other biological signals, as well as non-biological signals.

The computing device 150 can be a computer, tablet, mobile device, field programmable gate array (FPGA), microcontroller, or any other suitable device for processing information or instructions. The computing device 150 can be local to the user or can include components that are non-local to the user including one or both of the processor 152 or memory 154 (or portions thereof). For example, in at least some embodiments, the user may operate a terminal that is connected to a non-local computing device. In other embodiments, the memory 154 can be non-local to the user.

The computing device 150 can utilize any suitable processor 152 including one or more hardware processors that may be local to the user or non-local to the user or other components of the computing device. The processor 152 is configured to execute instructions such as instructions provided as part of a tag identification (ID) engine 155 stored in the memory 154.

Any suitable memory 154 can be used for the computing device 150. The memory 154 illustrates a type of computer-readable media, namely computer-readable storage media. Computer-readable storage media may include, but is not limited to, volatile, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 156 can be any suitable display device, such as a monitor, screen, or the like, and can include a printer. In some embodiments, the display is optional. In some embodiments, the display 156 may be integrated into a single unit with the computing device 150, such as a tablet, smart phone, or smart watch. In at least some embodiments, the display is not local to the user. The input device 158 can be, for example, a keyboard, mouse, touch screen, track ball, joystick, voice recognition system, or any combination thereof, or the like. In at least some embodiments, the input device is not local to the user.

The magnetic field generator(s) 162 can be, for example, Helmholtz coils, solenoid coils, planar coils, saddle coils, electromagnets, permanent magnets, or any other suitable arrangement for generating a magnetic field. As an example, the magnetic field generator 162 can include three orthogonal sets of coils to generate magnetic fields along three orthogonal axes. Other coil arrangements can also be used. The optional sensor(s) 164 can include, but are not limited to, one or more position sensors, orientation sensors, accelerometers, image recorders, or the like or any combination thereof.

The one or more magnetometers 160 can be any suitable magnetometer including, but not limited to, any suitable optically pumped magnetometer. Arrays of magnetometers are described in more detail herein. In at least some embodiments, at least one of the one or more magnetometers (or all of the magnetometers) of the system is arranged for operation in the SERF mode. Examples of magnetic field measurement or recording systems or methods of making such systems or components for such systems are described in U.S. Patent Application Publications Nos. 2020/0072916; 2020/0056263; 2020/0025844; 2020/0057116; 2019/0391213; 2020/0088811; 2020/0057115; 2020/0109481; 2020/0123416; 2020/0191883; 2020/0241094; 2020/0256929; 2020/0309873; 2020/0334559; 2020/0341081; 2020/0381128; 2020/0400763; US 2021/0011094; 2021/0015385; 2021/0041512; 2021/0041513; and 2021/0063510; U.S. patent application Ser. No. 17/087,988, and U.S. Provisional Patent Application Ser. Nos. 62/689,696; 62/699,596; 62/719,471; 62/719,475; 62/719,928; 62/723,933; 62/732,327; 62/732,791; 62/741,777; 62/743,343; 62/747,924; 62/745,144; 62/752,067; 62/776,895; 62/781,418; 62/796,958; 62/798,209; 62/798,330; 62/804,539; 62/826,045; 62/827,390; 62/836,421; 62/837,574; 62/837,587; 62/842,818; 62/855,820; 62/858,636; 62/860,001; 62/865,049; 62/873,694; 62/874,887; 62/883,399; 62/883,406; 62/888,858; 62/895,197; 62/896,929; 62/898,461; 62/910,248; 62/913,000; 62/926,032; 62/926,043; 62/933,085; 62/960,548; 62/971,132; 62/983,406; 63/031,469; 63/052,327; 63/076,015; 63/076,880; 63/080,248; 63/089,456; 63/135,364; 63/136,093; 63/136,415; 63/140,150; 63/158,700; 63/159,823; and 63/170,892, all of which are incorporated herein by reference in their entireties. In at least some embodiments, instead of, or in addition to, OPMs, other magnetometers or magnetic field sensors, such as SQUIDs, can be used.

Figure 1B:
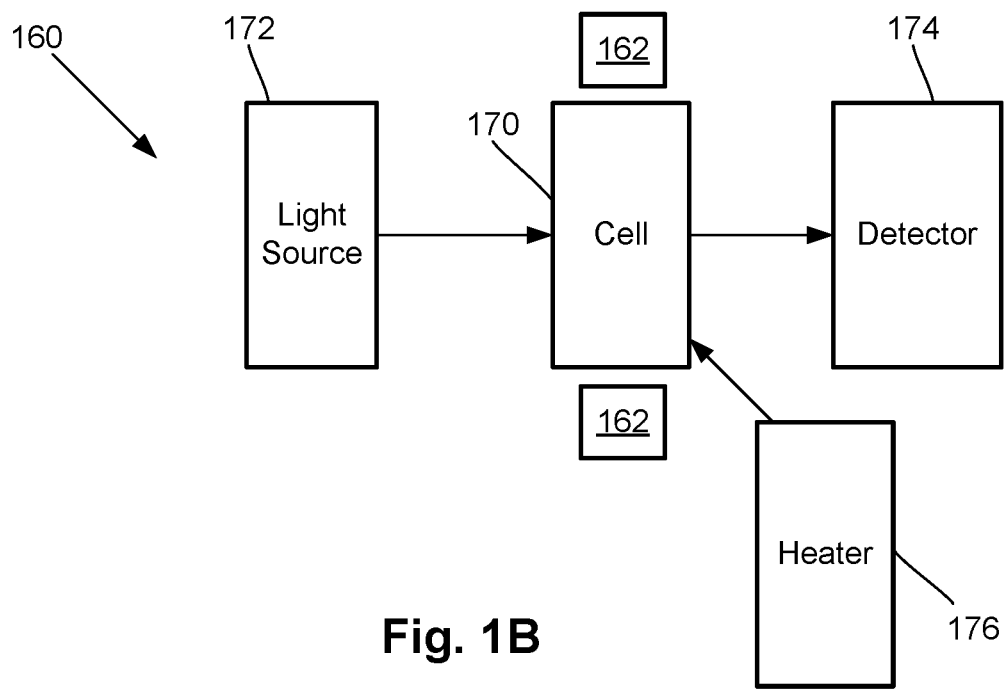
FIG. 1B is a schematic block diagram of one embodiment of a magnetometer, according to the invention.

FIG. 1B is a schematic block diagram of one embodiment of a magnetometer 160 which includes a vapor cell 170 (also referred to as a "cell" or a "gas cell") such as an alkali metal vapor cell; a heating device 176 to heat the cell 170; a light source 172; and a detector 174. In addition, coils of a magnetic field generator 162 can be positioned around the vapor cell 170. The vapor cell 170 can include, for example, an alkali metal vapor (for example, rubidium in natural abundance, isotopically enriched rubidium, potassium, or cesium, or any other suitable alkali metal such as lithium, sodium, or francium) and, optionally, one, or both, of a quenching gas (for example, nitrogen) or a buffer gas (for example, nitrogen, helium, neon, or argon). In some embodiments, the vapor cell may include the alkali metal atoms in a prevaporized form prior to heating to generate the vapor.

The light source 172 can include, for example, a laser to, respectively, optically pump the alkali metal atoms and probe the vapor cell. The light source 172 may also include optics (such as lenses, waveplates, collimators, polarizers, and objects with reflective surfaces) for beam shaping and polarization control and for directing the light from the light source to the cell and detector. Examples of suitable light sources include, but are not limited to, a diode laser (such as a vertical-cavity surface-emitting laser (VCSEL), distributed Bragg reflector laser (DBR), or distributed feedback laser (DFB)), light-emitting diode (LED), lamp, or any other suitable light source. In some embodiments, the light source 172 may include two light sources: a pump light source and a probe light source.

The detector 174 can include, for example, an optical detector to measure the optical properties of the transmitted probe light field amplitude, phase, or polarization, as quantified through optical absorption and dispersion curves, spectrum, or polarization or the like or any combination thereof. Examples of suitable detectors include, but are not limited to, a photodiode, charge coupled device (CCD) array, CMOS array, camera, photodiode array, single photon avalanche diode (SPAD) array, avalanche photodiode (APD) array, or any other suitable optical sensor array that can measure the change in transmitted light at the optical wavelengths of interest.

Figure 2:
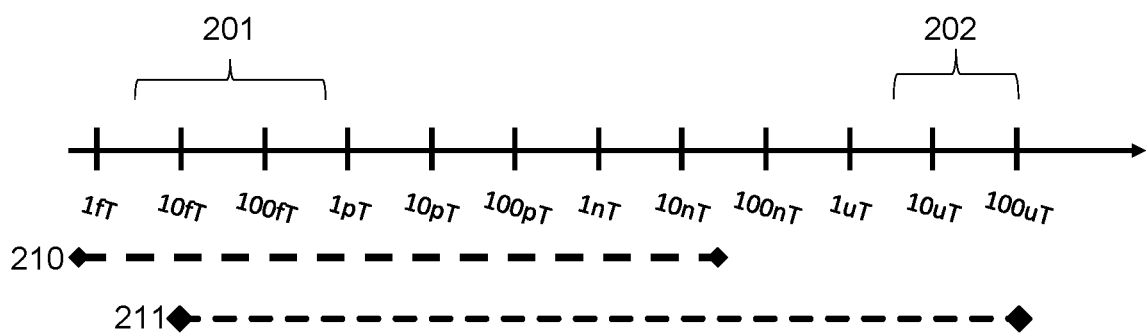
FIG. 2 shows a magnetic spectrum with lines indicating dynamic ranges of magnetometers operating in different modes.

FIG. 2 shows the magnetic spectrum from 1 fT to 100 μT in magnetic field strength on a logarithmic scale. The magnitude of magnetic fields generated by the human brain are indicated by range 201 and the magnitude of the background ambient magnetic field, including the Earth's magnetic field, by range 202. The strength of the Earth's magnetic field covers a range as it depends on the position on the Earth as well as the materials of the surrounding environment where the magnetic field is measured. Range 210 indicates the approximate measurement range of a magnetometer (e.g., an OPM) operating in the SERF mode (e.g., a SERF magnetometer) and range 211 indicates the approximate measurement range of a magnetometer operating in a scalar mode (e.g., a scalar magnetometer.) Typically, a SERF magnetometer is more sensitive than a scalar magnetometer, but many conventional SERF magnetometers typically only operate up to about 0 to 200 nT while the scalar magnetometer starts in the 10 to 100 fT range but extends above 10 to 100 μT.

U.S. Provisional Patent Application Ser. Nos. 63/031,469 and 63/076,015, both of which are incorporated herein by reference in their entireties, and other references cited herein describe systems and methods having a helmet or other headgear populated with an array of OPMs. This helmet or other headgear can be used in combination with a passively shielded enclosure, amenable for natural tasks, and active shielding. Passive shielding can attenuate environmental magnetic fields (e.g. the Earth's magnetic field, magnetic fields generated by power lines, etc.) to a level of 100 nT to 500 nT. Active shielding based on stationary coils provides further attenuation based on measurements of the residual ambient background magnetic field. Existing approaches to measure the residual ambient background magnetic field inside a passively shielded enclosure often rely on stationary sensors, which limits user motion to a range of a few centimeters. To extend user motion beyond this range, and enable a wider class of natural tasks, active shielding can be disposed in the passively shielded enclosure or associated with the OPM modules in the helmet or other headgear or any combination thereof. Systems and methods described herein can produce tracking information, such as motion or position of the helmet or orientation of the OPM sensors (or any combination thereof.) The multimodal sensing methods disclosed herein can provide this tracking information enabling system operation that is robust to user motion and use cases including user AR/VR interfaces for neural studies, correlation between user motion and neural signals, and subject compliance.

Figure 3:
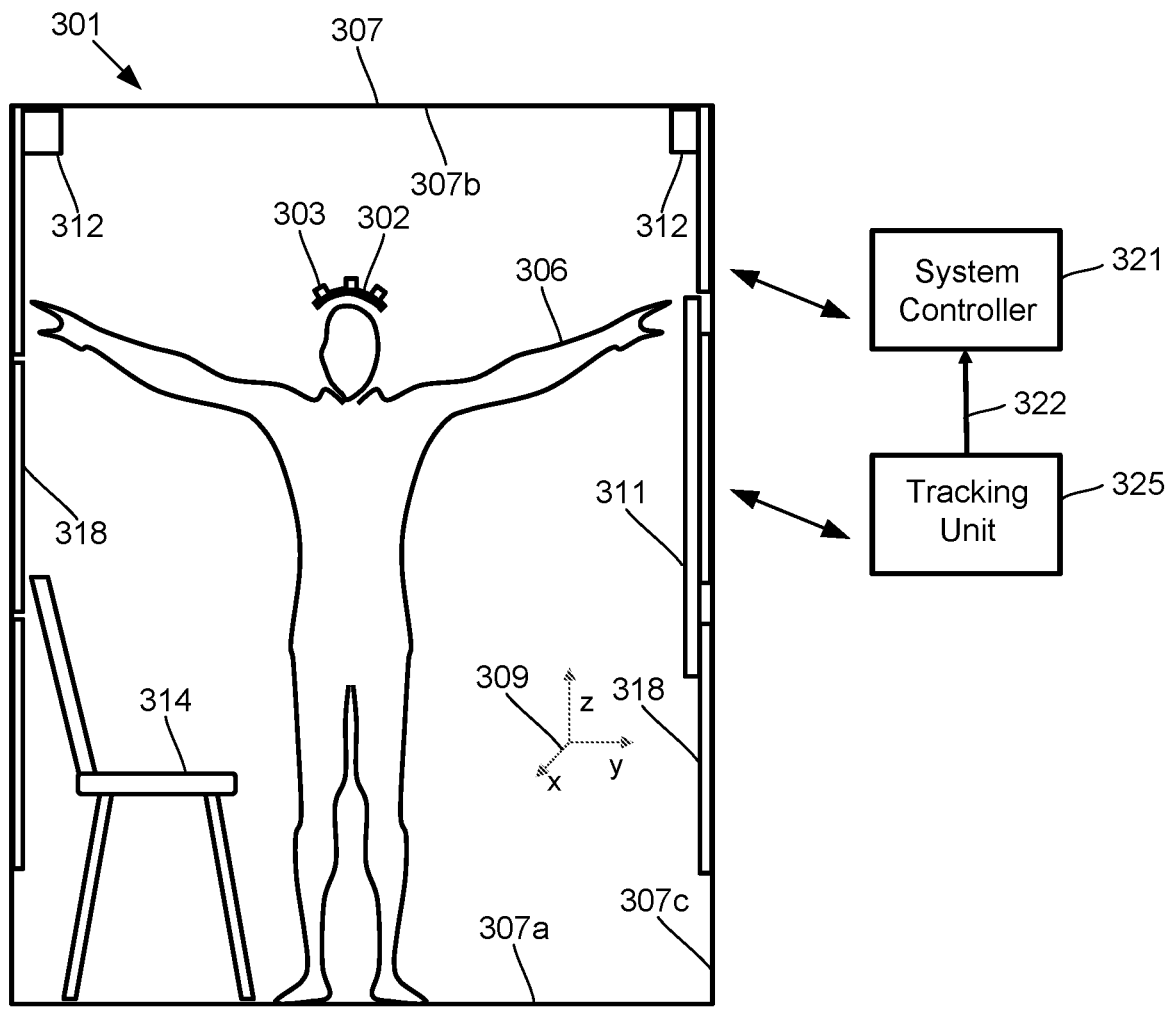
FIG. 3 is schematic side view of one embodiment of components of a magnetoencephalography (MEG) or other magnetic field measurement system including a passively shielded enclosure, according to the invention.

The systems and methods disclosed herein enable motion and pose tracking (for example, tracking of motion, position, orientation, or any combination thereof) within a magnetically shielded environment, such as a passively shielded enclosure. FIG. 3 illustrates a cross-sectional view of at least some components of one embodiment of a MEG or other magnetic field measurement or recording system 300 with a shielding arrangement 301. The user 306 is wearing a helmet 302 or other headgear populated with OPM modules 303. As described in more detail below, the helmet 302 may also be populated with inertial sensors or fiducial markers or any combination thereof. The user 306 may be free standing, seated in a chair 314, or sleeping.

The user 306 is in a magnetically shielded environment (MSE) formed by the shielding arrangement 301 to reduce the ambient background magnetic field for operation of the OPM modules 303 and measurement of neural signals using the OPM modules. The shielding arrangement 301 can be, for example, a combination of passive shielding, for example, a passively shielded enclosure 307 (such as a passively shielded room), and optional active shielding for reduction of the residual ambient background magnetic field by, for example, active shield coils 318 (e.g., electromagnetic coils) positioned, for example, on the inside of the exterior walls of the passively shielded enclosure 307. Active shielding can also, or instead, include active shield coils in the helmet or other headgear.

The passively shielded enclosure 307 can be made using passive shielding material, such as mu-metal or permalloy, or any other suitable material that reduces the ambient background magnetic field within the passively shielded enclosure. In at least some embodiments, the passively shielded enclosure 307 can be a room and can include a floor 307a, a ceiling 307b, and one or more vertical walls 307c extending from the floor to the ceiling. Each of the floor 307a, ceiling 307b, and vertical wall(s) 307c can include the passive shielding material.

In at least some embodiments, an active shield controller 324 is coupled to the active shield coils 318 to control the further reduction in the ambient background magnetic field within the passively shielded enclosure 307. In at least some embodiments, the active shield controller 324 has multiple channels with one or more of the active shield coils 318 coupled to each channel. For example, there can be two, three, four, six, eight, ten, twelve, 15, 20, 25, or more channels and two, four, six, eight, ten, twelve, 15, 20, 25, 30, 32, 40, 50, 60, 64, 70, 80, 90, 100, 120, 128, or more active shield coils. In at least some embodiments, two or more of the channels are independently operable meaning that operation of the independent channels does not depend on the other channels. In at least some embodiments, the active shield coils 318 are conductive wire or conductive traces and may be mounted on a substrate, such as a printed circuit board substrate.

In at least some embodiments, the user 306 can experience audio/visual stimulus from a screen or monitor 311 with or without sound generation capability. The MEG or other magnetic field measurement or recording system can use the measured neural signals to provide feedback based on the audio/visual stimulus. Alternatively or additionally, the MEG or other magnetic field measurement or recording system can also include one or more peripheral input devices (not shown) to provide feedback from a user based on the audio/visual stimulus through one or more of the following: spoken response, movement, touch, or any other suitable mechanism. Examples of peripheral input devices include, but are not limited to, microphones, joysticks, hand-held controllers or the like, a mouse, buttons, cameras (for example, to detect eye motion, gaze direction, blinking, facial expression, hand or limb movement, or the like or any combination thereof), biometric devices (for example, to detect heart rate, respiration rate, skin conductivity, or the like or any combination thereof), or the like or any combination thereof. In at least some embodiments, the large dynamic range of the OPMs allows for the use of peripheral input devices or other devices which may have an associated active magnetic field due to electrical currents in the peripheral device or passive fields due to ferromagnetic materials such as nickel or iron.

In at least some embodiments, user movement is monitored through one or a combination of two or more sensing modalities including, but not limited to, optical tracking 312, magnetic tracking (for example, implemented through the OPM modules 303 or other magnetic tracking units), or inertial tracking or the like.

In prior MEG methods and systems using OPMs, user motion tracking and sensor pose was estimated using a single sensing modality. Disadvantages of these prior systems and methods may include the following: First, the tracking system was limited by the intrinsic drawbacks of the given sensing modality, such as, for example, occlusion and illumination for optical modalities and magnetic disturbance and interference with OPMs for magnetic modalities. Second, motion tracking and sensor pose information was used off-line, either as part of a post signal-processing step or as a pre-calibration step. This approach is not compatible with use cases that utilize tracking information synchronously as the MEG recording takes place, such as, for example, closed-loop neural-feedback, augmented reality (AR), or virtual reality (VR) applications.

Furthermore, these prior methods and systems did not use inertial sensors, such as, gyroscopes and accelerometers. Although inertial sensors have been used in motion capture systems their deployment in MEG systems and methods is challenging due to their inherent drift, bias, and noise. Inertial Sensors often use reference vectors (for example, the Earth's gravity and magnetic field vector) for determining absolute orientation heading reference (a reference with respect to which orientation can be reported, for example, a heading 15 degrees north). Typically, these drawbacks are tackled by combining inertial measurements with vector measurements of Earth's field, for orientation reference, and GPS and maps for positioning. The systems and methods disclosed herein are amenable for incorporating inertial sensors without the need for measurement of the Earth's magnetic field or GPS or maps.

In at least some embodiments, a tracking arrangement utilizing one, two, or more of the sensing modalities may also be used to track the pose (motion, position, or orientation or any combination thereof) of the helmet 302 and OPM modules 303 with respect to each other and with respect to a global stationary reference coordinate system 309. In at least some embodiments, the stationary reference coordinate system 309 can be that of the electromagnetic coils 318, the walls of the passively shielded enclosure 307, optical tracking devices 112, or any other point of reference inside the passively shielded enclosure 307, such as furniture, e.g., the chair 314 or the screen or monitor 311. In at least some embodiments, the relative motion, position, or orientation of the helmet 302 or OPM modules 303 to a particular starting position or orientation (or base position or orientation) can be provided instead of, or in addition to, the absolute motion, position, or orientation relative to the global stationary reference coordinate system 309.

A tracking unit 325 for tracking control and processing can control tracking using the one, two, or more sensing modalities to infer the motion of user 306, as well as the pose (e.g., position or orientation or both) of the user 306, helmet 302, or OPM modules 303 or any combination thereof. In at least some embodiments, the sensor modalities can be utilized synchronously with recordings of magnetic (e.g., neural) signals measured using the OPM modules. Motion and pose information 322 can be transmitted to a system controller 321.

In at least some embodiments, as the user moves (or the user's head moves), the active shield controller 324, in communication with the system controller 321 or tracking unit 325, alters the magnetic fields generated by the active shield coils 318 to control the reduction in the ambient background magnetic field around the helmet 302 and OPM modules 303. In at least some embodiments, the residual ambient background magnetic field after reduction using the active shield coils 318 is not uniform within the passively shielded enclosure 307, but instead there is a region with the lowest residual ambient background magnetic field that can be shifted or moved, using the active shield controller 324 and in response to the detection of user movement by the one or more sensing modalities. In at least some embodiments, this region can be moved, using the active shield controller 324 to alter the magnetic fields generated by the active shield coils 318, so that the region remains at or near the helmet 302 and OPM modules 303.

Figure 5A:
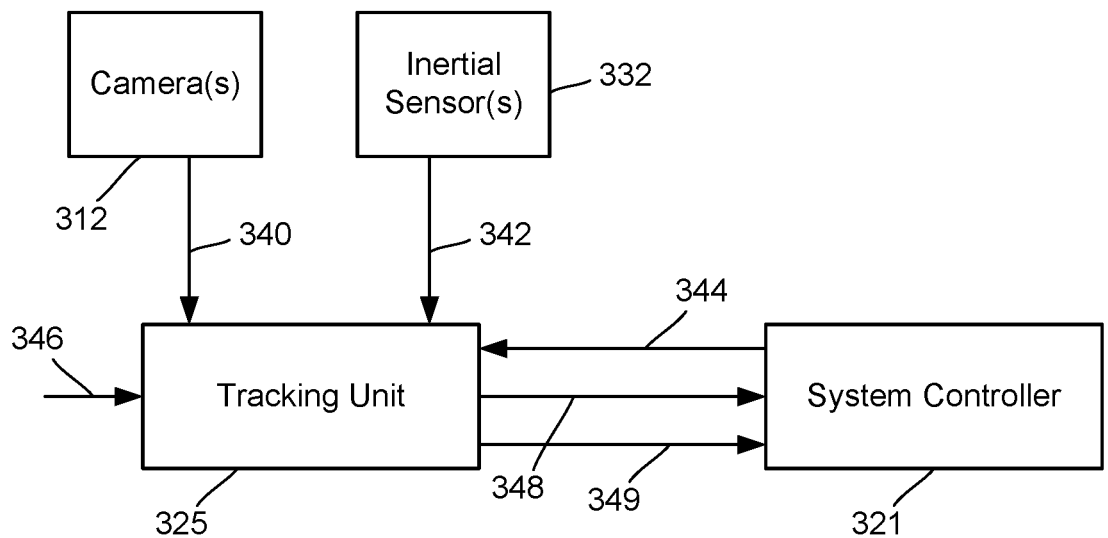
FIG. 5A is a block diagram of portions of the tracking arrangement and magnetoencephalography (MEG) or other magnetic field measurement system of FIG. 4A, according to the invention.
Figure 5B:
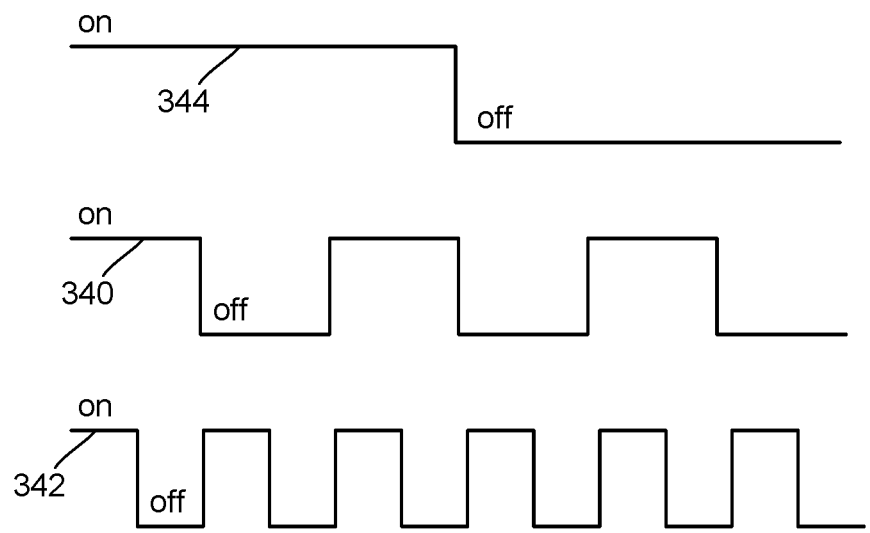
FIG. 5B is one embodiment of a timing diagram for a magnetic data stream, optical data stream, and inertial data stream for the tracking arrangement of FIG. 4A.

FIGS. 4A, 4B, and 4C illustrate embodiments of a system or method for user motion tracking using a combination of two or more sensing modalities, including but not limited to, magnetic tracking, optical tracking, or inertial tracking. In addition, FIG. 5A is a diagram of the integration of data streams 340, 342, 344 from optical tracking (for example, camera(s) 312), inertial tracking (for example, inertial sensors 332), and magnetic tracking (using magnetic field tones 319 (FIG. 4A) generated by the active shield coils 318 or other magnetic field generators and operated by the system controller 321), respectively, into a tracking unit 325 for control and processing. Each data stream 340, 342, 344 may have its own data rate, as illustrated in FIG. 5B. In at least some embodiments, the magnetic data stream 344 has the slowest data rate, the optical data stream 340 has a higher data rate, and the inertial data stream 342 has the fastest data rate. There may be other data stream(s) 346. The tracking unit 325 can provide pose information 322 (e.g., position or orientation or both) and may also provide visual metadata 348, particularly from camera(s) 312.

In at least some embodiments, a pose and user motion tracking system includes any combinations of the following: optical tracking; magnetic tracking; inertial tracking with inertial sensors; the use of machine vision, facial recognition, or motion capture to track facial features of a user 306; a tracking unit 325 capable of processing and consumption of pose information synchronously with MEG measurements; the estimation of the location of the brain of the user 306 with respect to the helmet 302 using real-time optical measurements; or the use of Kalman filters to merge the data streams 340, 342, 344.

Returning to FIG. 4A, in at least some embodiments, the magnetic sensing modality tracks the response of one, two, or more OPM modules 303 to magnetic field tones 319 applied using one or more of the active shield coils 318, as illustrated in FIG. 4A. In some embodiments, instead of, or in addition to, using one or more of the OPM modules 303, magnetic field sensors positioned in the helmet 302 or user 306 can be used for motion tracking. In some embodiments, instead of, or in addition to, using one or more of the active shield coils 318, other electromagnetic coils or magnetic field generators can be used to generate the magnetic field tones.

As an example, a magnetic tracking data stream 344 can provide position or orientation information by applying spatially homogeneous magnetic field tones 319 using the active shield coils 318 or other electromagnetic coils or magnetic field generators. The magnetic field tones 319, b(t), are described in the global reference frame x-y-z 309 (FIG. 3) by $$b_g(t) = b_x \cos(\omega_x t)\hat{x} + b_y \cos(\omega_y t)\hat{y} + b_z \cos(\omega_z t)\hat{z}$$

while the tones measured in the coordinate frame x'-y'-z' of a given OPM module 303 or other magnetic field sensor are $$b_s(t) = b_{x'}(t)\hat{x}' + b_{y'}(t)\hat{y}' + b_{z'}(t)\hat{z}'$$

where the projection of the tones along the x' axis of the OPM module or other magnetic field sensor is given by $$b_{x'}(t) = r_{x'x} b_x \cos(\omega_x t) + r_{x'y} b_y \cos(\omega_y t) + r_{x'z} b_z \cos(\omega_z t)$$

and similar for $b_{y'}(t)$ and $b_{z'}(t)$. In this case, $r_{ij}$ are the elements of the rotation matrix $R_{rot}$ mapping the orientation of the given OPM module 303 or other magnetic field sensor with respect to the global reference frame 309 (FIG. 3):

$$b_s(t) = R_{rot} b_g$$

As seen from the expression above the matrix elements $r_{ij}$ are mapped to the amplitude of sensor outputs $b_{x'}(t)$, $b_{y'}(t)$, and $b_{z'}(t)$ at the known tone frequencies $\omega_x$, $\omega_y$, and $\omega_z$. Therefore, $r_{ij}$ can be obtained using, for example, narrow-band measurement techniques such as lock-in detection, nonlinear regression methods, by fast-Fourier transforms, or any other adequate method of spectral analysis. In some embodiments, the matrix elements $r_{ij}$ may be compared to earlier measurements of the same matrix elements to determine relative motion of the helmet 302 or user 306. In some embodiments, the matrix elements $r_{ij}$ may be used to provide an absolute orientation or position of the helmet 302 or user 306 in the global reference frame 309 (FIG. 3).

In at least some embodiments, the frequency of the magnetic field tones 319 can have a frequency in the range of, for example, 1 Hz to 200 Hz and an amplitude in the range of, for example, 10 pT up to 1/10 of the linewidth of the zero-field resonance of the OPMs of the OPM modules 303 which itself can range from 10 nT to 100 nT depending on operating conditions. This range offers implementation versatility and reduces or minimizes magnetic disturbances to MEG or other biomagnetic measurements. In at least some embodiments, to further avoid interference with MEG measurements the magnetic field tones 319 can be applied from time to time while MEG recording is off or not active. As an example, the magnetic field tones 319 may be initiated every 20 seconds for a duration of, for example, 0.1 second to 1, 2, or 3 or more seconds. In at least some embodiments, the system does not measure MEG signals during the period of time in which the magnetic field tones 319 are presented.

In at least some embodiments, the magnetic field tones 319 may have a relatively high frequency to reduce interference with the neural or other biomagnetic signals that are present. Such magnetic field tones 310 may be presented continuously or periodically. For example, if the spectrum of the MEG recording (i.e., the spectrum of the neural or other biomagnetic signals) spans a frequency range from, for example, DC (i.e., 0 Hz) to 100 Hz then relatively high-frequency magnetic field tones 319 with a frequency or frequencies above this range, for example, above 100 Hz or at or above 150, 200, 250, 500, or 1000 Hz, can be presented.

In at least some embodiments, the optical sensing modality includes at least one source 315 of light that illuminates the user 306. One, two, or more cameras 312 or other light detectors collect light 317 reflected, or directed, from the user 306, helmet 302, or OPM modules 303 or from one or more fiducial markers 330 (such as those illustrated in FIG. 4B) which are placed on the helmet 302, OPM modules 303, or user 306 (for example, on the face or body of the user for facial or body tracking). Any suitable camera 312 or other light detector can be used including, but not limited to, depth cameras, infra-red cameras, or thermal cameras or any combination thereof. Examples of fiducial markers 330 include chess boards 330a, squares 330b, or any other suitable marker, such as markers used in the field of machine vision or motion capture. In at least some embodiments, specific physical features of the helmet 302 or OPM modules 303 can be the fiducial markers 330. For instance, the physical package of the OPM module 303 can be used as a fiducial marker 330.

The camera(s) 312 or other light detectors can be mounted in the passively shielded enclosure 307 or free-standing or any combination thereof. In other embodiments, the camera(s) 312 can be mounted on the helmet 302 and user 306 and fiducial markers 330 positioned on or within the passively shielded enclosure 307.

In at least some embodiments, the fiducial markers 330, helmet 302, OPM modules 303, or any combination thereof may be the light sources. For example, the fiducial markers 330, helmet 302, OPM modules 303, or any combination thereof can include emitting sources of infrared light (or other wavelengths of light), such as LEDs or laser diodes, that the camera(s) 312 can track when light is emitted by the fiducial markers 330, helmet 302, OPM modules 303, or any combination thereof.

The optical tracking modality may also, or instead, use markerless features of the user's body, as illustrated in FIG. 4C, including, but not limited to, the nose 306a, left eye 306b, right eye 306c, mouth 306d, left hand 306e, right hand 306f, or other body part or the like. The user features can also allow the camera(s) 312 to track the relative pose (e.g., position or orientation) of the user's head with respect to the helmet 302 for user compliance (e.g., for correct wearing of the helmet 302 at the start and during the MEG recording) and head-to-helmet coregistration (e.g., for determining the position of the OPM modules 303 relative to the head during the MEG recording) or the like. In at least some embodiments, these features can be extracted from the optical data stream 340 using methods from machine vision, facial recognition, or other methods for fast, online analysis of images.

The optical data stream 340 may also provide visual metadata 348, such as user facial or body expressions or changes, that may be useful for interpreting the MEG measurements (e.g., the neural or other biomagnetic signals.)

The tracking unit 325 uses the optical data stream 340 (for example, images collected with the camera(s) 312) to infer, determine, or estimate the position or orientation (of both) of the fiducial marker(s) 330 or user's facial or body features with respect to the camera(s) 312. In at least some embodiments, depending on the camera(s) used, images can be collected at a frame rate ranging from, for example, 10 FPS to 100 FPS. The images are processed in the tracking unit 325 using, for example, machine vision, facial recognition, motion capture, or other suitable algorithms that detect and track known features in the fiducial marker 330 (for instance the four corners of a square fiducial marker 330a, 330b), helmet 302, or OPM modules 303; the user's facial or body features; the light emission by light emitting fiducial markers 330, helmet 302, or OPM modules 303; or the like or any combination thereof.

Using the known distance between tracked features or light emission, the position of the features or light emission in the 2D image, and optionally a camera calibration matrix or the like (describing distortions introduced by the camera to the image), the position and orientation of the fiducial markers or user's facial or body features with respect to the camera(s) is estimated. In at least some embodiments, a sensor calibration step (described below) can be used to provide a reference of the pose of the fiducial marker(s) 330 or user 306 with respect to the helmet 302 and the pose of the camera(s) 312 with respect to the global reference system 309 (FIG. 3). In at least some embodiments, the fiducial marker(s) 330 is rigidly attached to the helmet 302 and the camera(s) 312 is stationary with respect to the reference system x-y-z 309. Therefore, the changes in the pose of the helmet 302 with respect to reference system 309 can be accessed via the changes in the pose of the fiducial marker(s) 330 or user's facial or body features with respect to the camera(s) 312 as presented in the optical data stream 340.

In the inertial tracking modality, one or more inertial sensors 332, such as gyroscopes (for example, a 3-axis gyroscope) or accelerometers (such as a 3-axis accelerometer) or any combination thereof, are rigidly attached to the helmet 302 or the user 306 to track the angular velocity or linear acceleration or both of the helmet or user.

In at least some embodiments, the inertial data stream 342 utilizes signals from one or more inertial sensors 332 to infer the rate of change in the orientation or position (or both) of the helmet 302 or user 306. In at least some embodiments, the inertial data stream 342 can complement or overcome some of the shortcomings of optical or magnetic sensing, such as occlusion or magnetic interference. Gyroscopes and accelerometers are capable of outputting measurements at rates ranging from, for example, 100 Hz to 500 Hz which, at least in some embodiments, is faster than rates for the magnetic or optical data streams. This may provide faster pose information in at least some control applications. In at least some embodiments, to obtain the change in orientation and position with time the system can integrate the output of the gyroscope or double integrate the output of the accelerometer. In at least some embodiments, absolute orientation or position (or both) with respect to the global reference frame 309 is determined by the tracking unit 325 by merging the inertial data stream 342 with one or both of the magnetic data stream 344 or optical data stream 340. For example, magnetic field tones 319 applied from time to time can provide an absolute reference for the orientation vector at time to and the optical data stream 401 can provide the absolute position and velocity at time to.

Figure 6:
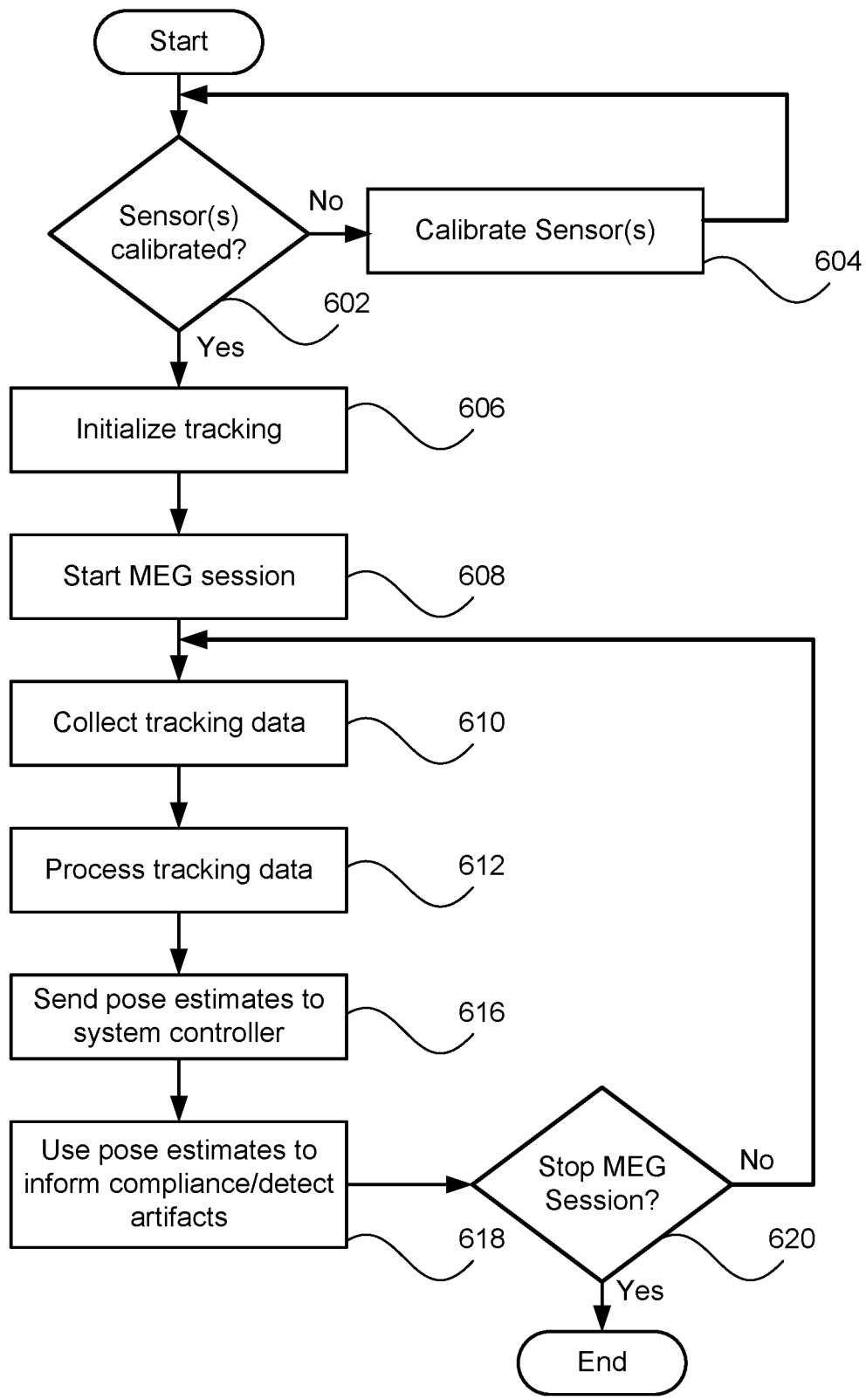
FIG. 6 is a flowchart of one embodiment of a method for tracking a helmet or user of a MEG or other magnetic field measurement or recording system, according to the invention.

FIG. 6 is a flowchart or a workflow of one embodiment of a method for tracking a helmet 302 or user 306 of a MEG or other magnetic field measurement or recording system. The flowchart or workflow illustrates one embodiment of the operation of a tracking system using sensors of two or more sensing modalities.

In step 602, the system determines if the sensor(s) of the sensing modalities (e.g., the camera(s), inertial sensor(s), and magnetic field detector(s) such as OPM(s)) have been calibrated. In step 604, the sensors are calibrated. This can include calibration of OPM modules 303 or other magnetic field detectors as used in magnetic tracking, calibration of camera(s) 312 or other light detectors as used in optical tracking and the registration of the pose of the camera reference frame with respect to the global reference system 309. This can also include the registration of the reference frames of OPM modules 303, inertial sensor(s) 332, or fiducial markers 330 with respect to the reference frame of the helmet 302 or global reference system 309. Step 604 may be repeated as needed including repetition during the MEG session.

In step 606, tracking is initialized which may include determining an initial pose (e.g., position or orientation or both) of the helmet 302 or user 306. Calibration parameters as well as any relevant prior information is passed to the tracking unit 325. At this point the user 306 is wearing the helmet 302.

In step 608, the MEG (or other magnetic field detection) session starts. The OPM sensors 303 are used to record MEG or other biomagnetic signals. In at least some embodiments, the user 306 is free to move within the confines of passively shielded enclosure 307 or to move the user's head.

In step 610, tracking data is collected and provided to the tracking unit 325. In at least some embodiments, optical and inertial data can be recorded continually or periodically. In at least some embodiments, the magnetic data is recorded periodically if the magnetic field tones 319 may interfere with the recording of MEG or other biomagnetic signals by the OPM modules 303. In other embodiments, the magnetic data can be recorded continually if the magnetic field tones 319 do not interfere with the recording of MEG or other biomagnetic signals by the OPM modules 303.

In step 612, the optical, inertial, or magnetic data streams 340, 342, 344 (whichever are used in the tracking system) are processed in the tracking unit 325 to provide pose estimates 322. In at least some embodiments, the pose estimates 322 can include, for example, position, orientation, or motion (or any combination thereof) of the helmet 302 or user 306 in the global reference frame 309 or in the reference frame of the helmet.

In step 616, the pose estimates 322 is sent to the system controller 321. Any additional metadata 348 collected from video recording means is sent to the system controller 321. In optional step 618, the pose estimates 322 can be used to inform whether the user 306 is in compliance with helmet 302 use and wearing requirements and may also inform of possible detected bio-magnetic artifacts.

In step 620, the system determines of the MEG session is to be stopped and, if so, the MEG session ends. If not, the MEG session continues to repeat steps 610, 612, 616, 618, and 620 until the MEG session ends.

In at least some embodiment, the multimodal sensing approach to motion and pose tracking described herein enables robust operation of OPMs in their linear range for a wider range of user motion. In at least some embodiment, the multimodal sensing approach described herein uses no additional effort to the user (for example, not attaching anything or wiring anything to the user other than the helmet). In at least some embodiment, the multimodal sensing approach described herein doesn't degrade the neural signals. In at least some embodiment, the multimodal sensing approach described herein allows collection of metadata, via the optical tracking modality, without increasing the complexity of the MEG measurement process.

The methods, systems, and units described herein may be embodied in many different forms and should not be construed as limited to the embodiments set forth herein. Accordingly, the methods, systems, and units described herein may take the form of an entirely hardware embodiment, an entirely software embodiment or an embodiment combining software and hardware aspects. The methods described herein can be performed using any type of processor or any combination of processors where each processor performs at least part of the process.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification provides a description of the invention and its manufacture and use. Since many embodiments of the invention can be made without departing from the spirit and scope of the invention, the invention also resides in the claims hereinafter appended.

What is claimed as new and desired to be protected by Letters Patent of the United States is:

1. A magnetic field recording system, comprising:
a headgear configured to be placed on a user;
a plurality of optically pumped magnetometers (OPMs) disposed in or on the headgear and configured to detect magnetic fields;
at least two sensing modalities selected from the following:
i) a magnetic sensing modality comprising at least one electromagnetic coil configured to produce magnetic field tones at one or more frequencies and at least one magnetic field sensor configured for placement on the user to detect the magnetic field tones and to produce a magnetic data stream,
ii) an optical sensing modality comprising at least one light source and at least one camera or light detector configured to receive light reflected or directed from the user and to produce an optical data stream, or
iii) an inertial sensing modality comprising at least one inertial sensor configured for placement on a user and to produce an inertial data stream; and
a tracking unit configured to receive, from each of the at least two sensing modalities, the corresponding magnetic data stream, optical data stream, or inertial data stream and to track a position or orientation of the headgear or user; and
a system controller configured to control operation of the OPMs and to receive, from the tracking unit, the position or orientation of the headgear or user.

2. The magnetic field recording system of claim 1, wherein the at least two sensing modalities comprise the inertial sensing modality.

3. The magnetic field recording system of claim 1, wherein the at least two sensing modalities comprise the magnetic sensing modality, the optical sensing modality, and the inertial sensing modality.

4. The magnetic field recording system of claim 1, further comprising a passively shielded enclosure comprising a plurality of walls defining the passively shielded enclosure, each of the plurality of walls comprising passive magnetic shielding material to reduce an ambient background magnetic field within the passively shielded enclosure.

5. The magnetic field recording system of claim 4, further comprising a plurality of active shield coils distributed within the passively shielded enclosure and configured to further reduce the ambient background magnetic field within the passively shielded enclosure.

6. The magnetic field recording system of claim 5, wherein at least one of the active shield coils is at least one of the at least one electromagnetic coil configured to produce the magnetic field tones.

7. The magnetic field recording system of claim 1, wherein the at least one electromagnetic coil is configured to produce the magnetic field tones having a frequency of at least 100 Hz.

8. The magnetic field recording system of claim 1, wherein the optical sensing modality comprises at least one fiducial marker for placement on the user, the headgear, or the OPM modules and configured to reflect light from the at least one light source.

9. The magnetic field recording system of claim 8, wherein the at least one fiducial marker is disposed on the headgear or the OPM modules.

10. The magnetic field recording system of claim 1, wherein at least one of the at least one light source is a fiducial marker for placement on the user, the headgear, or the OPM modules and configured to emit light.

11. The magnetic field recording system of claim 1, wherein the tracking unit is configured to utilize at least one of the OPM modules as a fiduciary marker for the optical sensing modality.

12. The magnetic field recording system of claim 1, wherein the tracking unit is configured to utilize at least one feature of the user as a fiduciary marker for the optical sensing modality.

13. The magnetic field recording system of claim 1, wherein each of the at least one inertial sensor is an accelerometer or a gyroscope.

14. A method of recording biomagnetic fields using the magnetic field recording system of claim 1, the method comprising:
  disposing the headgear on the user;
  tracking the position or orientation of the user, headgear, or OPM modules using the at least two sensing modalities and the tracking unit;
  recording the biomagnetic fields using the OPMs; and
  associating the biomagnetic fields with biological regions of the user using the tracked position or orientation.

15. The method of claim 14, wherein recording the biomagnetic fields comprises recording the biomagnetic fields at individual first periods of time, wherein the at least two sensing modalities comprise the magnetic sensing modality, wherein tracking the position or orientation of the user comprises generating the magnetic field tones using the at least one electromagnetic coil at second periods of time between the periods of time.

16. The method of claim 14, wherein the at least two sensing modalities comprise the magnetic sensing modality, wherein tracking the position or orientation of the user, headgear, or OPM modules comprises generating the magnetic field tones at a frequency of at least 100 Hz using the at least one electromagnetic coil.

17. The method of claim 16, wherein generating the magnetic field tones occurs, at least in part, simultaneously with recording the biomagnetic fields.

18. The method of claim 14, wherein the at least two sensing modalities comprises the optical sensing modality, wherein tracking the position or orientation of the user, headgear or OPM modules comprises receiving light reflected or directed from the user at the at least one camera or light detector, wherein receiving the light occurs, at least in part, simultaneously with recording the biomagnetic fields.

19. The method of claim 14, wherein the at least two sensing modalities comprises the inertial sensing modality, wherein tracking the position or orientation of the user, headgear or OPM modules comprises producing an inertial data stream using the at least one inertial sensor, wherein producing the inertial data stream occurs, at least in part, simultaneously with recording the biomagnetic fields.

20. The method of claim 14, wherein associating the biomagnetic fields with biological regions of the user comprises sending estimates of the position or orientation of the user, headgear, or OPM modules from the tracking unit to the system controller.

* * * * *